(12) United States Patent
Chen et al.

(10) Patent No.: US 8,648,297 B2
(45) Date of Patent: Feb. 11, 2014

(54) COUPLING OF LIQUID CHROMATOGRAPHY WITH MASS SPECTROMETRY BY LIQUID SAMPLE DESORPTION ELECTROSPRAY IONIZATION (DESI)

(75) Inventors: Hao Chen, The Plains, OH (US); Yun Zhang, Athens, OH (US); Zongqian Yuan, Shanghai (CN); Howard Dewald, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 13/553,145

(22) Filed: Jul. 19, 2012

(65) Prior Publication Data
US 2013/0023005 A1 Jan. 24, 2013

Related U.S. Application Data

(60) Provisional application No. 61/510,197, filed on Jul. 21, 2011.

(51) Int. Cl.
*H01J 49/26* (2006.01)

(52) U.S. Cl.
USPC .................... 250/288; 250/281; 250/282

(58) Field of Classification Search
USPC ........ 250/281, 282, 288; 210/635, 656, 198.2
See application file for complete search history.

(56) References Cited

U.S. PATENT DOCUMENTS

| | | | |
|---|---|---|---|
| 3,997,298 A | 12/1976 | McLafferty et al. | |
| 4,861,988 A | 8/1989 | Henion et al. | |
| 5,879,949 A | 3/1999 | Cole et al. | |
| 6,952,013 B2 | 10/2005 | Granger et al. | |
| 7,335,897 B2 | 2/2008 | Takats et al. | |
| 7,525,105 B2 | 4/2009 | Kovtoun | |
| 7,544,933 B2 | 6/2009 | Cooks et al. | |
| 7,687,772 B2 | 3/2010 | Shiea | |
| 7,714,281 B2 | 5/2010 | Musselman | |
| 7,718,958 B2 | 5/2010 | Shiea et al. | |
| 7,723,678 B2 | 5/2010 | Truche et al. | |
| 7,750,291 B2 | 7/2010 | Shiea | |
| 7,772,548 B2 | 8/2010 | Wollnik | |
| 7,915,579 B2 * | 3/2011 | Chen et al. ............... 250/288 |
| 8,330,119 B2 * | 12/2012 | Chen et al. ............... 250/425 |
| 2005/0230635 A1 | 10/2005 | Takats et al. | |
| 2006/0273254 A1 | 12/2006 | Berkout et al. | |
| 2007/0221835 A1 | 9/2007 | Raftery et al. | |
| 2008/0047330 A1 * | 2/2008 | Whitehouse et al. ........ 73/61.48 |
| 2008/0179511 A1 | 7/2008 | Chen et al. | |
| 2008/0265152 A1 | 10/2008 | Bateman | |
| 2009/0095899 A1 | 4/2009 | Whitehouse et al. | |

(Continued)

OTHER PUBLICATIONS

F. Zhou and GJ Van Berkel, "Electrochemistry Combined On-Line with Electrospray Mass Spectrometry." Anal. Chem. (1995) 67:3643-3649.

(Continued)

*Primary Examiner* — Nicole Ippolito
(74) *Attorney, Agent, or Firm* — Wood, Herron & Evans, LLP

(57) ABSTRACT

An apparatus to separate and analyze components of a liquid sample include a high performance liquid chromatograph with a mass spectrometer utilizing desorption electrospray ionization. This permits separation and evaluation of different components in a liquid sample. Further, this can be combined with online derivation via reactive DESI and, further, can be used with further electrochemistry.

12 Claims, 21 Drawing Sheets

(56) References Cited

U.S. PATENT DOCUMENTS

| | | |
|---|---|---|
| 2009/0189069 A1 | 7/2009 | Chen et al. |
| 2009/0309020 A1 | 12/2009 | Cooks et al. |
| 2010/0044560 A1 | 2/2010 | Basile et al. |
| 2010/0059674 A1* | 3/2010 | Chen et al. .................. 250/288 |
| 2010/0078550 A1 | 4/2010 | Wiseman et al. |
| 2010/0140468 A1 | 6/2010 | Musselman |

OTHER PUBLICATIONS

C.F. Bökman, et al., "A Setup for the Coupling of a Thin-Layer Electrochemical Flow Cell to Electrospray Mass Spectrometry." Anal. Chem. (2004) 76(7):2017-2024.

Z. Miao and H. Chen, "Analysis of Continuous-Flow Liquid Samples by Desorption Electrospray Ionization Mass Spectrometry (DESI-MS)." Proc. 56th Ann. Am. Soc. Mass Spectrom. Conf. Denver, CO, Jun. 1-5, 2008.

Zhixin Miao and Hao Chen, "Direct Analysis of Liquid Samples by Desorption Electrospray Ionization-Mass Spectrometry (DESI-MS)", J. Am. Soc. Mass Spectrom., 2009, 20, 10-19.

Z. Takáts, et al., "Electrosonic Spray Ionization. A Gentle Technique for Generating Folded Proteins and Protein Complexes in the Gas Phase and for Studying Ion-Molecule Reactions at Atmospheric Pressure." Anal. Chem. (2004) 76:4050-4058.

C.C. Mulligan, et al., "Fast Analysis of High-Energy Compounds and Agricultural Chemicals in Water with Desorption Electrospray Ionization Mass Spectrometry." Rapid Comm. Mass Spectrom. (2007) 21:3729-3736.

H. Chen, et al., "Extractive Electrospray Ionization for Direct Analysis of Undiluted Urine, Milk, and Other Complex Mixtures without Sample Preparation." Chem. Comm. (2006) 2042-2044.

Hambitzer and J. Heitbaum, "Electrochemical Thermospray Mass Spectrometry." Anal. Chem. (1986) 58:1067-1070.

M. Barber, et al., "Fast Atom Bombardment Mass Spectrometry." Anal. Chem. (1982) 54:645A-657A.

A. Bond, et al., "A Role for Electrospray Mass Spectrometry in Electrochemical Studies." Anal. Chem. (1995) 67: 1691-1695.

H. Deng, et al., "Electrochemically Modulated Liquid Chromatography Coupled with On-Line Electrospray Mass Spectrometry." Anal. Chem. (2000) 72: 2641-2647.

W. Lu, et al. "On-line Linear Sweep Voltammetry-Electrospray Mass Spectrometry." Anal. Chem.(1997) 69:2478-2484.

H.P. Permentier and A.P. Bruins, "Electrochemical Oxidation and Cleavage of Proteins with On-Line Mass Spectrometric Detection: Development of an Instrumental Alternative to Enzymatic Protein Digestion." J. Am. Soc. Mass Spectrom. (2004) 15:1707-1716.

Y. Zhang and H. Chen, "Detection of saccharides by reactive desorption electrospray ionization (DESI) using modified phenylboronic acids." J. Int. Mass Spectrom., (2010) 289: 98-107.

X Ma, M Zhao, Z Lin, S Zhang, C Yang, X Zhang, Versatile Platform Employing Desorption Electrospray Ionization Mass Spectrometry for High-Throughput Analysis, Anal. Chem. 80(15) (2008) 6131.

* cited by examiner

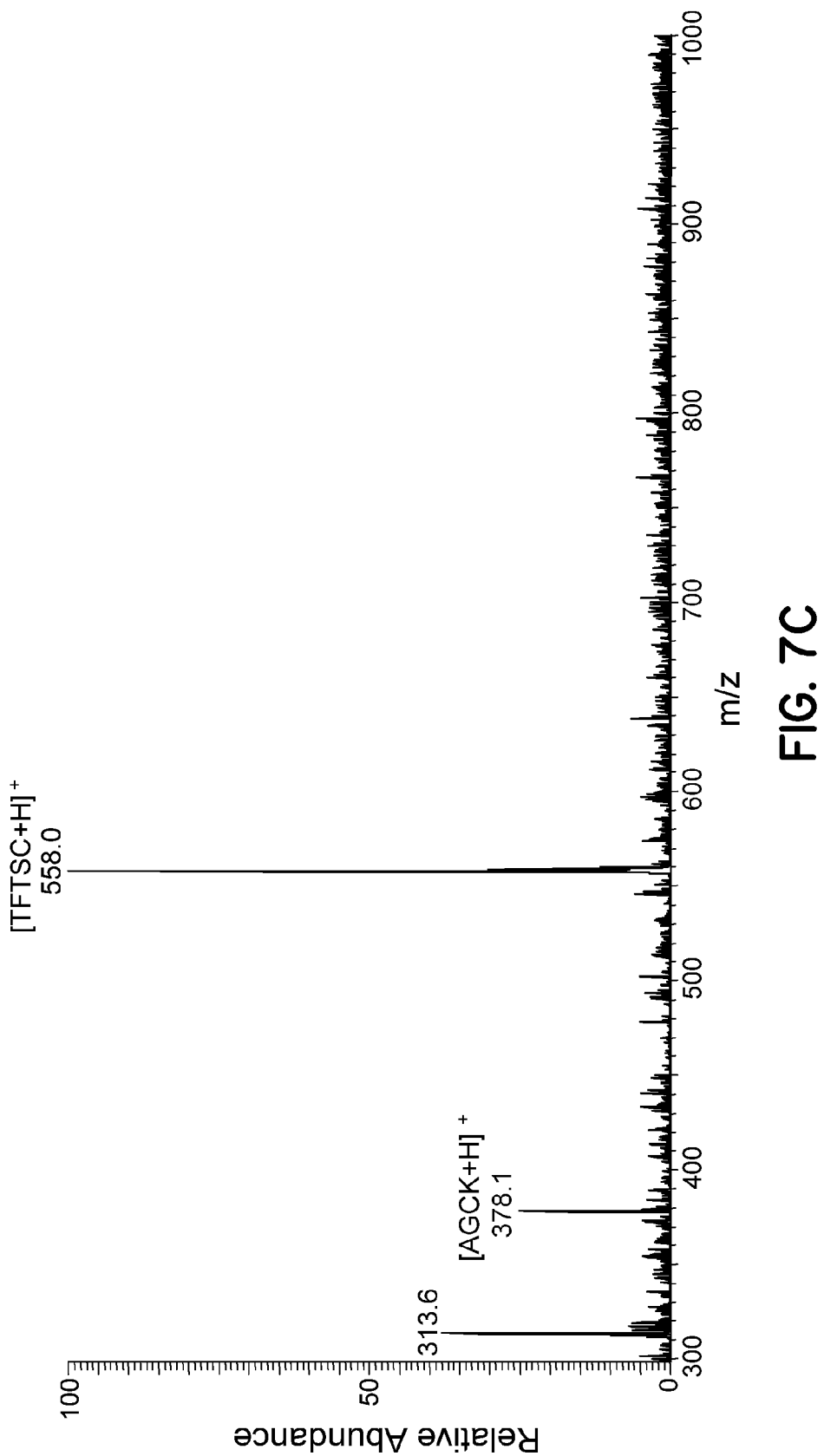

COUPLING OF LIQUID CHROMATOGRAPHY WITH MASS SPECTROMETRY BY LIQUID SAMPLE DESORPTION ELECTROSPRAY IONIZATION (DESI)

RELATED APPLICATION

This application is related to and claims the benefit of U.S. Provisional Patent Application Ser. No. 61/510,197, filed on Jul. 21, 2011, the disclosure of which is incorporated herein by reference.

TECHNICAL FIELD

The present invention is related to apparatii for coupling liquid chromatography (LC) with mass spectrometry (MS) and methods of using the same.

BACKGROUND

Ambient mass spectrometry is a recent advancement in the field of analytical chemistry and has allowed for the analysis of samples with little-to-no sample preparation. Based on this concept, a variety of ambient ionization methods have been introduced, including desorption electrospray ionization (DESI), direct analysis in real time (DART), desorption atmospheric pressure chemical ionization (DAPCI), electrospray-assisted laser desertion/ionization (ELDI), matrix-assisted laser desorption electrospray ionization (MALDESI), extractive electrospray ionization (EESI), atmospheric solids analysis probe (ASAP), jet desorption ionization (JeDI), desorption sonic spray ionization (DeSSI), desorption atmospheric pressure photoionization (DAPPI), plasma-assisted desorption ionization (PADI), and dielectric barrier discharge ionization (DBDI).

DESI is a representative method for ambient mass spectrometry. It has been shown to be useful in providing a rapid and efficient means of desorbing and ionizing a variety of target compounds of interest under ambient conditions. A variety of analytes (for example, pharmaceuticals, metabolites, drugs of abuse, explosives, chemical warfare agents, and biological tissues) have all been studied with these ambient ionization methods.

In U.S. Pat. No. 7,915,579, DESI has been shown to analyze liquid samples without sample preparation and may be used for ionizing both small molecules and large biomolecules, such as proteins. Still, it would be useful to use the liquid DESI apparatus in combination with liquid chromatography for the analysis of mixtures; however, the high flow rates associated with some chromatography techniques, such as high performance liquid chromatography ("HPLC"), tend to overwhelm the conventional ion source, such as electrospray ionization (ESI).

Furthermore, after analyte separation by chromatography, some analytes are difficult to ionize; therefore, it is often necessary to include post-column derivatization. Typically, the protocol for derivatization is to introduce a chemical reagent solution that merges with the chromatographic eluent via a Tee mixer. Such a mixing causes an increased time delay for MS ionization, leading to peak broadening resulting from diffusion effects.

In addition, integration of electrochemical cells into a LC/MS system will broaden the application of LC/MS. Conventionally, the coupling of EC with MS has been accomplished with ionization methods such as thermospray (TS), fast atom bombardment (FAB), and electrospray ionization (ESI). In particular, the latter method is useful in ionizing non-volatile products or intermediates of electrochemical reactions. However, in coupling EC with ESI, the EC system needs to be electrically floated, or decoupled, from the ionization source to separate the high voltage operation of the ionization source from the low voltage operation of the EC cell. This decoupling increases the complexity of the apparatus and the methods of analysis. Also, in coupling EC with ESI-MS there is a limitation that the solvent for electrolysis in EC must be compatible with ESI ionization. The combination of DESI with the EC system has been shown in U.S. patent application Ser. No. 12/558,819, published as Application Publication No. 2010/0258717, the disclosure of which is incorporated herein by reference in its entirety.

Still, there remains a need for improving the performance of LC/MS to tolerate high flow elution rate of LC without a limitation in selecting a solvent for LC mobile phase and electrolysis, online post-column derivatization, and easy integration of EC cells into the LC/MS systems for broader application.

SUMMARY OF THE INVENTION

The present invention is premised upon the realization that liquid chromatography can be coupled with mass-spectrometry using desorption electrospray ionization (DESI). DESI provides a versatile interface which allows a wide range of elution flow rates online derivatization via reactive DESI and, further, combination with electrochemistry.

The objects and advantages of the present invention will be further appreciated in light of the following detailed description and drawings, in which:

BRIEF DESCRIPTION OF THE FIGURES

FIGS. 7B and 7C are DESI-MS prepared according to the method of Example 3; and

DETAILED DESCRIPTION

Figure 1:
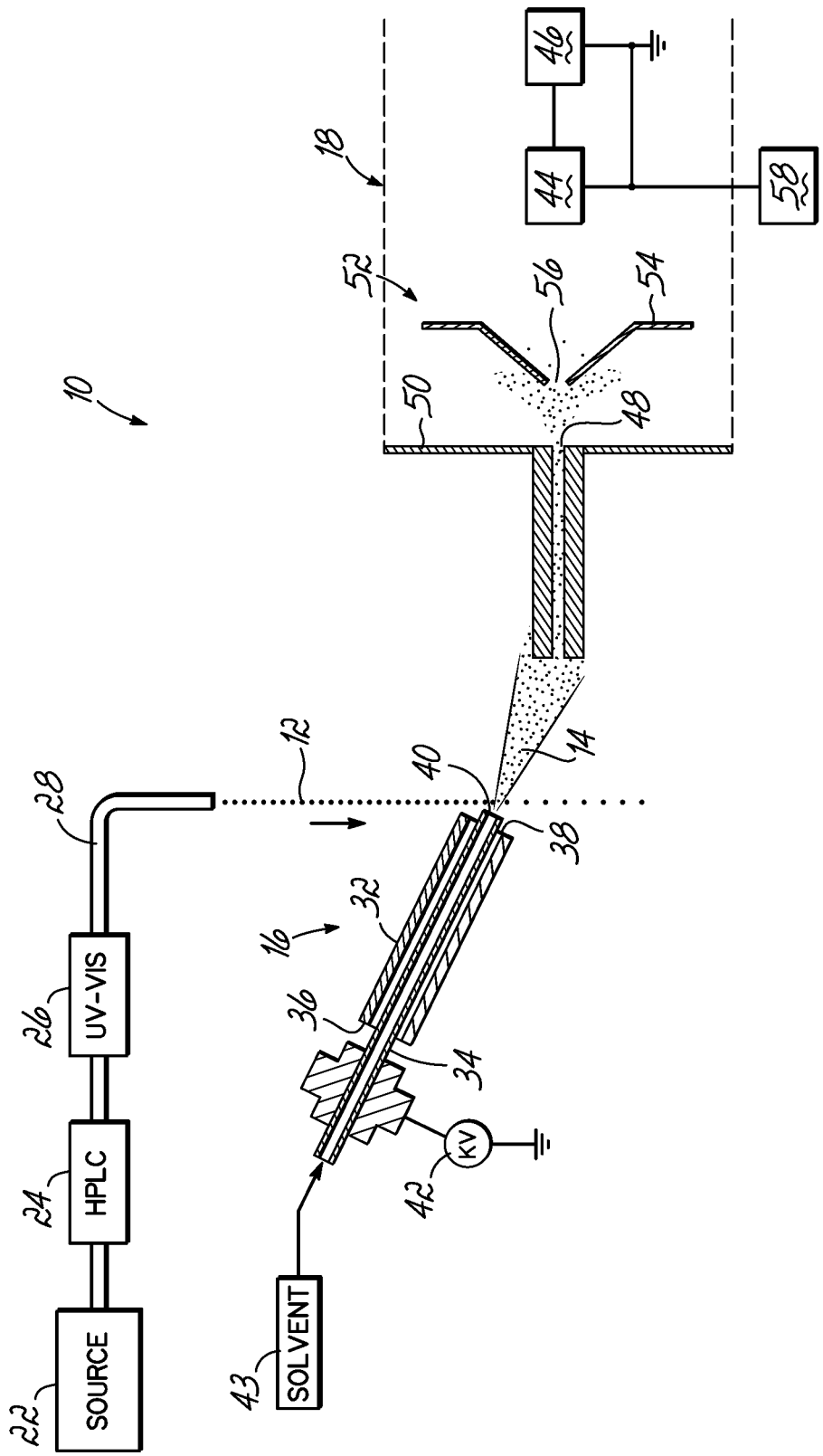
FIG. 1 is a diagrammatic depiction of the present invention.

The liquid sample desorption electrospray ionization mass-spectrometry (LS-DESI-MS) apparatus was described in detail in U.S. Pat. No. 7,915,579, the disclosure of which is incorporated in its entirety herein by reference. Briefly, FIG. 1 illustrates the LS-DESI-MS apparatus 10 where an analyte from a liquid sample 12 is ionized by desorption of the analytes by a charged and nebulized solvent 14 generated and emitted from a nebulizing ionizer 16 under ambient conditions. The LS-DESI-MS apparatus 10 forms gas phase ions that can be analyzed by a mass spectrometer 18.

Operation of the LS-DESI-MS apparatus 10, as shown in FIG. 1, begins by providing a sample supplied from a sample supply (labeled as source 22) to a High-Performance Liquid Chromatograph ("HPLC 24"), which, though not shown, generally includes a pump and at least one liquid chromatography column that is configured to elute the sample as one or more fractions in accordance with the particular stationary phase of the chromatography column, as is known by those of ordinary skill in the art. Generally, the flow rate of the sample through the HPLC 24 ranges from about 0.01 mL/min to about 3 mL/min.

The fractions may then be directed into an Ultraviolet-Visible Spectrometer ("UV-Vis 26") where the absorption or transmittance, at a particular wavelength of light in the ultraviolet or visible range of the electromagnetic spectrum, of each fraction may be determined The amount of absorption or transmittance may be related to the presence and the amount of a particular analyte within the fraction.

The fractions may then pass into a tube 28 constructed from a non-reactive material, such as silica, stainless steel, or aluminum and that is configured to generate a continuous jet of the liquid sample 12. While the dimensions of the tube 28 may vary, in some embodiments the tube 28 may have an inner diameter ranging from about 0.05 mm to about 0.1 mm.

At least a portion of the continuous jet of liquid sample 12 may then be desorbed by the charged and nebulized solvent 14 emitted from the nebulizing ionizer 16. The nebulizing ionizer 16 may be a desorption electrospray ionization probe ("DESI probe") that includes a housing 32 having a solvent conduit 34 surrounded by a gas conduit 36; however, it would be understood that other ambient ionization apparatus may alternatively be used. An outlet 38 of the gas conduit 36 is positioned about 0.1 mm to about 0.2 mm proximally to an outlet 40 of the solvent conduit 34. The solvent conduit 34 can be constructed from a fused silica capillary with an inner diameter ranging from about 50 μm to about 100 μm. The gas conduit 36 can also be a fused silica capillary with an inner diameter that is generally larger than the outer diameter of the solvent conduit 34, i.e., typically about 0.25 mm; however, these dimensions should not be considered limiting.

A voltage generator 42 is operable to charge the solvent within the solvent conduit 34.

In using the DESI probe 16, a solvent 43 is supplied to the solvent conduit 34. While the particular solvent 43 used is dependent on the chemical nature of the liquid sample 12 in study, one example of an appropriate solvent mixture can be methanol and water with either 0.5% or 1% acetic acid, v/v, which is injected at a rate of about 5 μL/min to about 10 μL/min. A gas, typically an inert gas such as $N_2$, is supplied to the gas conduit 36 at pressures ranging from about 8 bar to about 15 bar. The voltage generator 42 is activated and provides a voltage potential, typically ranging from about −5 kV to about 5 kV, to the solvent 43. This generates an electrically-charged solvent within the solvent conduit 34.

The now electrically-charged solvent traverses the solvent conduit 34 to the solvent conduit outlet 40. There, the charged solvent is impacted by the surrounding high-pressure gas leaving the gas conduit outlet 38. This high-pressure gas causes the flow of the charged solvent to be nebulized into a spray of the charged and nebulized solvent 14, which then impacts the continuous jet of the sample 12. This impact will cause desorption and ionization of a portion of the sample 12 into the mass spectrometer 18. It will be readily appreciated that the angle by which the nebulized solvent 14 impacts the sample 12 may be varied to increase the likelihood of the liquid sample 12 entering the mass spectrometer 18.

While not wishing to be bound by theory, it is believed that the mechanism by which the nebulized solvent 14 interacts with the sample 12 and desorbs at least a portion of the sample 12 may be chemical sputtering, charge transfer, or droplet pick-up, with the most likely of these mechanisms being droplet pick-up. During droplet pick-up, the nebulized solvent 14 interacts with the sample 12 to yield desorbed secondary charged droplets containing analyte. The secondary charged droplet will then undergo desolvation to yield ions of the analyte, i.e., gas phase ions.

The nebulizing ionizer 16 is interfaced to a cavity of the mass spectrometer 18, which includes a mass filter 44 and the mass detector 46 maintained at vacuum. This interface can aid in desolving the solvent from the secondary charged droplet to form the ions of analyte. The ions of analyte enter the mass spectrometer 18 through an orifice 48 of a plate 50, which provides an opening into the mass spectrometer 18 while maintaining vacuum pressures. The ions of analyte are then directed to a skimmer 52, which can be constructed as a cone-shaped plate 54 having an orifice 56, and is operable to focus the ions of analyte into a narrow beam (not shown) as it enters the mass spectrometer 18. This skimmer 52 is typically grounded. In some embodiments, the mass spectrometer 18 can further include a separate focusing lens (not shown) between the skimmer 52 and the mass filter 44 to focus the ion beam and reduce the natural expansion of the ion beam by effusion through the orifice 56 of the skimmer 52.

After passing the skimmer 52, the ion beam is directed to the mass filter 44. Conventional mass filters 44 include time-of-flight, quadrupolar, sector, Orbitrap, FT-ICR or ion trap, which are operable to cause ions of analyte having a specified mass-to-charge (m/z) ratio to transverse the mass filter 44 and be quantified at the mass detector 46. One particularly suitable instrument is a Thermo Finnigan LCQ DECA or DECA MAX ion trap mass spectrometer (San Jose, Calif.).

For example, in operating a conventional quadrupole modality, an ion beam is directed through four parallel electrodes, wherein the four parallel electrodes are comprised of two pairs of electrodes. A radiofrequency field and a DC voltage potential are applied to each of the two pairs of electrodes by a power supply such that the two pairs differ in polarity of the voltage potentials. Only the ions within the ion beam having a particular m/z will continue through the parallel electrodes to the mass detector 56; that is, the ions will be equally attracted to and deflected by the two pairs of electrodes while the mean free path induced by the radiofrequency field onto the ion of analyte does not exceed distance between the electrodes. Thus, the ion of analyte having the particular m/z will balance the radiofrequency and DC voltage forces from the parallel electrodes, and will thereby traverse the parallel electrodes and impact the mass detector 46.

The $m_1/z_1$ ions that reach the mass detector 46, typically a Faraday plate coupled to a picoammeter, are measured as a current (I) induced by a total number (n) of ions impacting the mass detector 36 over a period of time (t) and in accordance with n/t=I/e, wherein e is the elementary charge.

The method continues with altering the operational conditions of the mass filter 44 such that ions having a second mass-to-charge ratio, $m_2/z_2$, will traverse the mass filter 44 and impact the mass detector 46 in the manner described. A spectrum may then be generated relating the relative abundances with respect to m/z of the ions detected.

Operation of the mass filter 44 and the mass detector 46 can be by way of a controller 58. A suitable controller 58 can be a standard PC computer; however, the present invention should not be considered so limited.

The use of the DESI probe 16 enables direct analysis of the continuous jet of the liquid sample 12 eluted from the HPLC 24 at a high flow rate whereas other ionization sources are unable to produce an ion signal due to flooding of the ion source.

Figure 2:
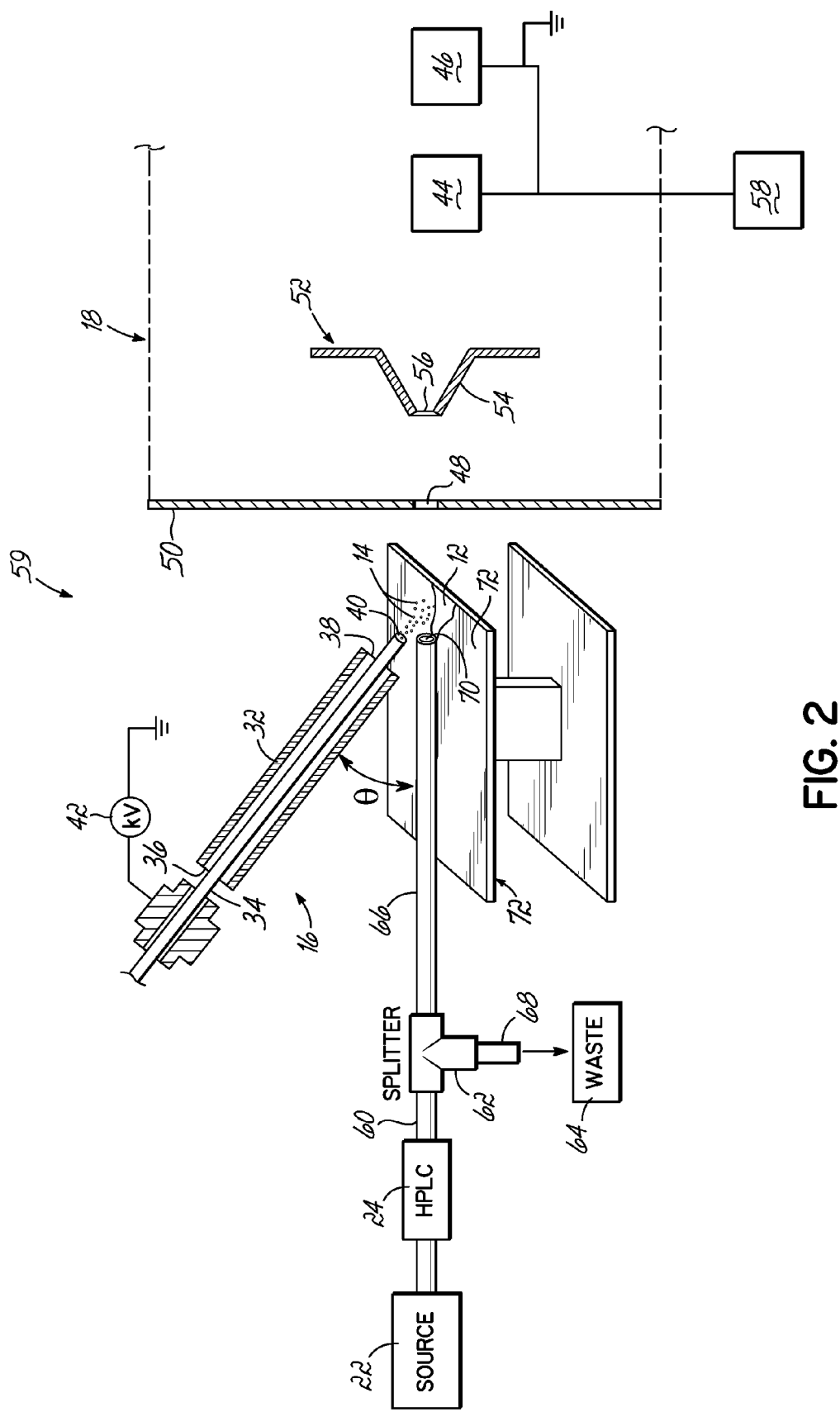
FIG. 2 is a diagrammatic depiction of an alternate embodiment of the present invention.

While the DESI probe 16 is capable of producing an ion signal at high sample flow rates, decreasing the flow rate may provide greater sensitivity. FIG. 2 illustrates another embodiment of a sample analysis system 59 wherein like reference numbers refer to like features in previous figures. In this embodiment, as the fraction elute from the column of the HPLC 24, the fractions enter a tube 60 having a splitter 62 therein that diverts a first portion of the fractions (i.e., the liquid sample 12) to a first tube 66, which is directed toward the nebulizing ionizer 16 and a second portion of the fractions to a second tube 68, which is directed to a waste container 64. The splitter 62 is adjustable such that the first portion may be adjusted relative to the second portion and in order to maximize the ion signal at the DESI probe 16.

More particularly, the fractions passing through the first tube 66 move to a distally located opening 70 of the tube 66 that is positioned on a sample surface 72. In the illustrative embodiment, the sample surface 72 includes a planar surface and can be constructed from any nonreactive material, such as polytetrafluoroethylene (PTFE). The design of the sample surface 72 can vary, but should be suitable to accommodate the tube 66 and the DESI probe 16. In this way, at least a portion of the liquid sample 12 can be desorbed off the planar surface and directed substantially toward the mass spectrometer 18 according to methods discussed in detail above. Though not specifically shown, the tube 66, which may be constructed in a manner that is similar the tube 28 of FIG. 1, may be affixed to the planar surface of the sample surface 72, such as by a clamp, which will prevent movement of the opening 70.

The second portion of the fractions enters the waste container 64 for proper disposal or other suitable labware for additional off-line analysis.

Figure 3:
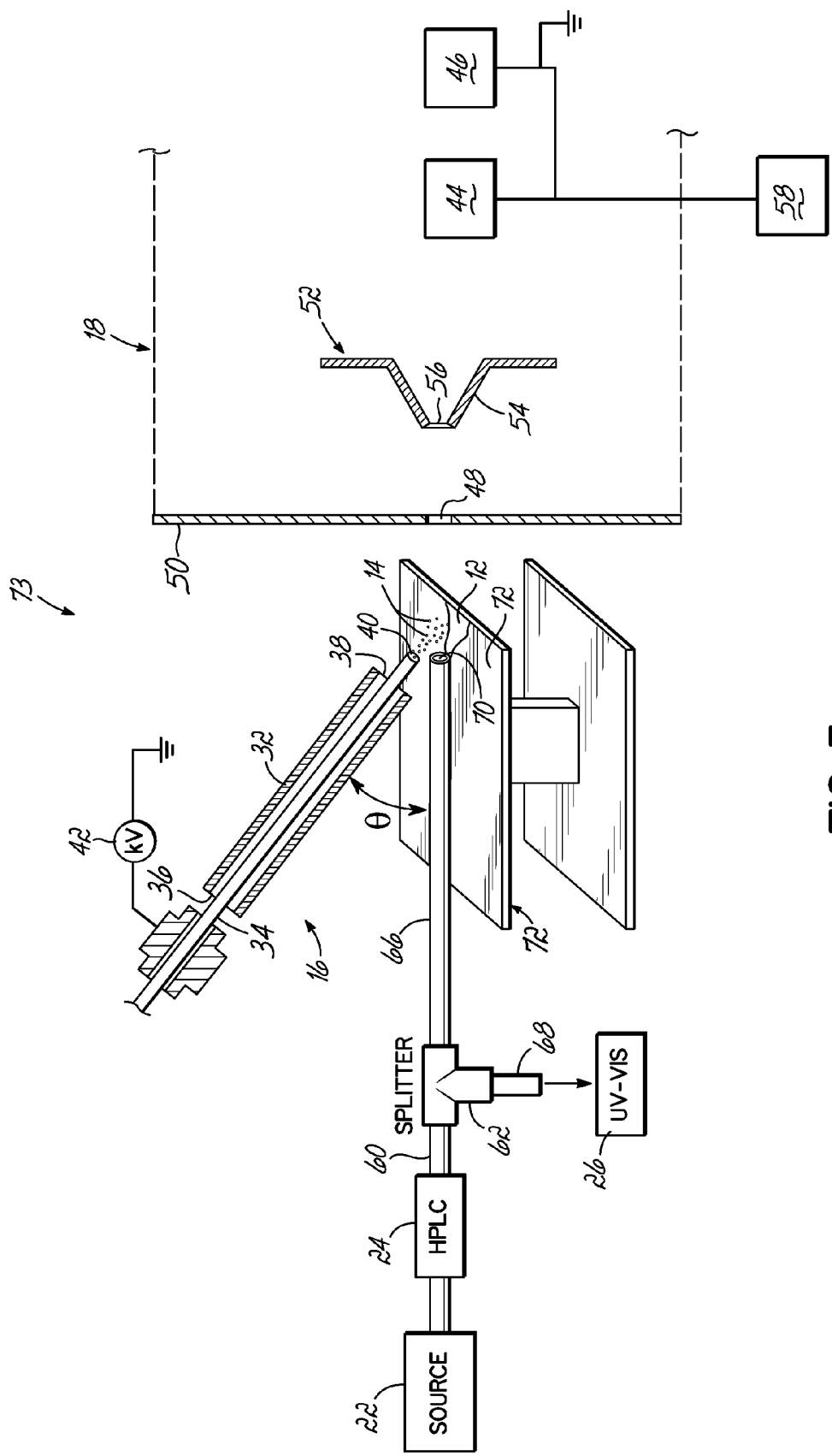
FIG. 3 is a diagrammatic depiction of a second alternate embodiment of the present invention.

FIG. 3 illustrates another embodiment of an analysis system 73 that is similar to the system 59 of FIG. 2 except that the second portion enters the UV-Vis 26 instead of the waste container 64. In this way, the analytes eluted from the columns may be analyzed nearly simultaneously using both UV-Vis and mass spectroscopies. Furthermore, it would be readily understood that the UV-Vis modality is readily adaptable to high sample flow rates that may be associated with the second portion of the fractions.

Often times a particular analyte cannot be ionized or may have an m/z value that overlaps with the m/z value of another analyte (which may or may not be of interest). Accordingly, the particular analyte may undergo a derivatization reaction to form a chemical derivative that improves detectability of the particular analyte. Derivatization reactions may include a variety of mechanisms, but should generally form only one product that is stable for at least the detection period, cause the particular analyte to undergo a complete reaction, and should not change the structure of the particular analyte. In some embodiments, a selected chemical reagent may be doped with the DESI spray solvent to allow online derivatization of analyte eluted from the LC column which takes place during DESI ionization.

Figure 4:
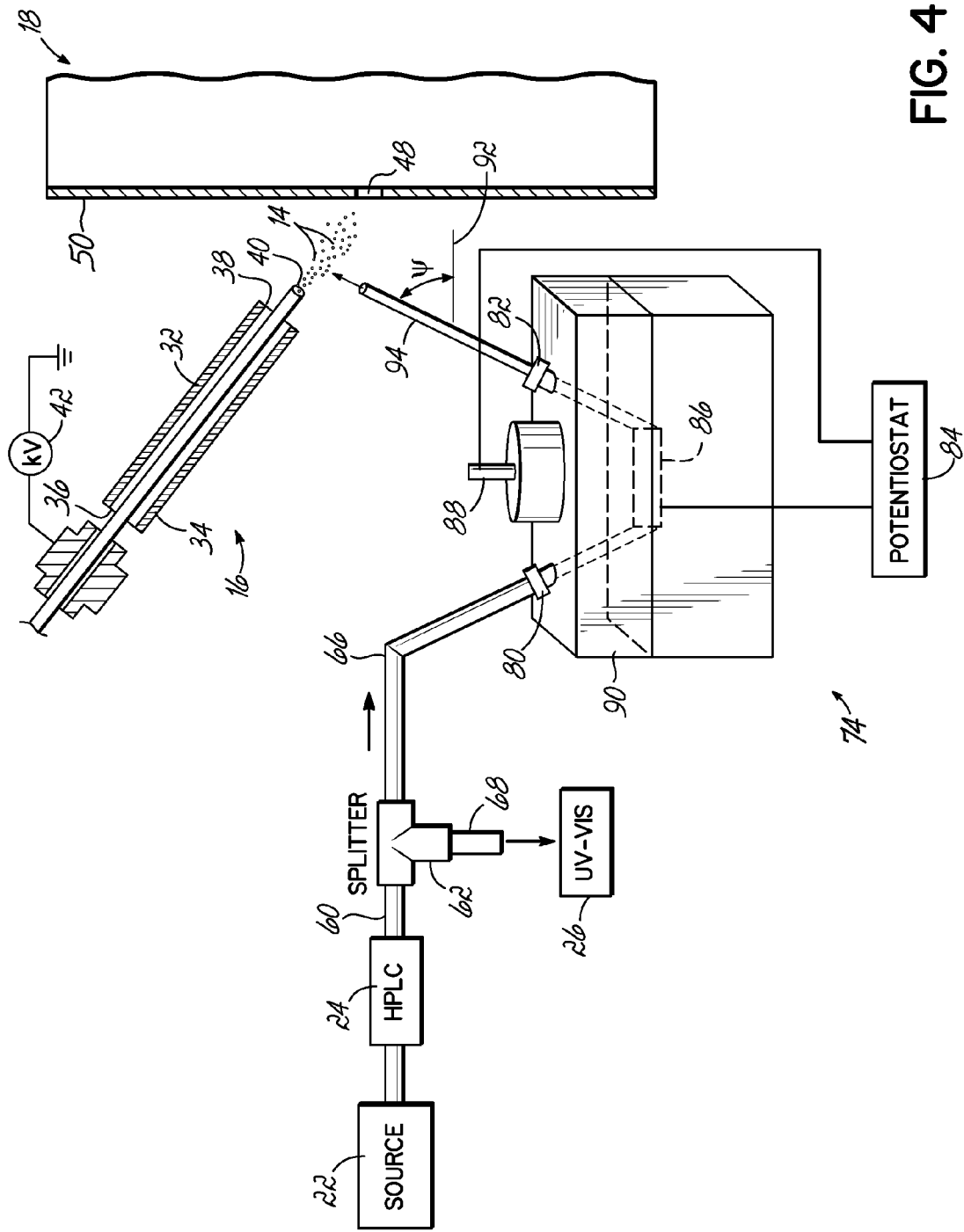
FIG. 4 is a diagrammatic depiction of a third alternate embodiment of the present invention utilizing an electrochemical cell.

Turning now to FIG. 4, wherein like reference numbers refer to like features in previous figures, an analytical system 74 in accordance with another embodiment is shown. Generally, the analytical system 74 is similar to the system 73 of FIG. 3 but further includes an electrochemical cell 74, which is positioned at a distal end of the first tube 66.

Figure 4A:
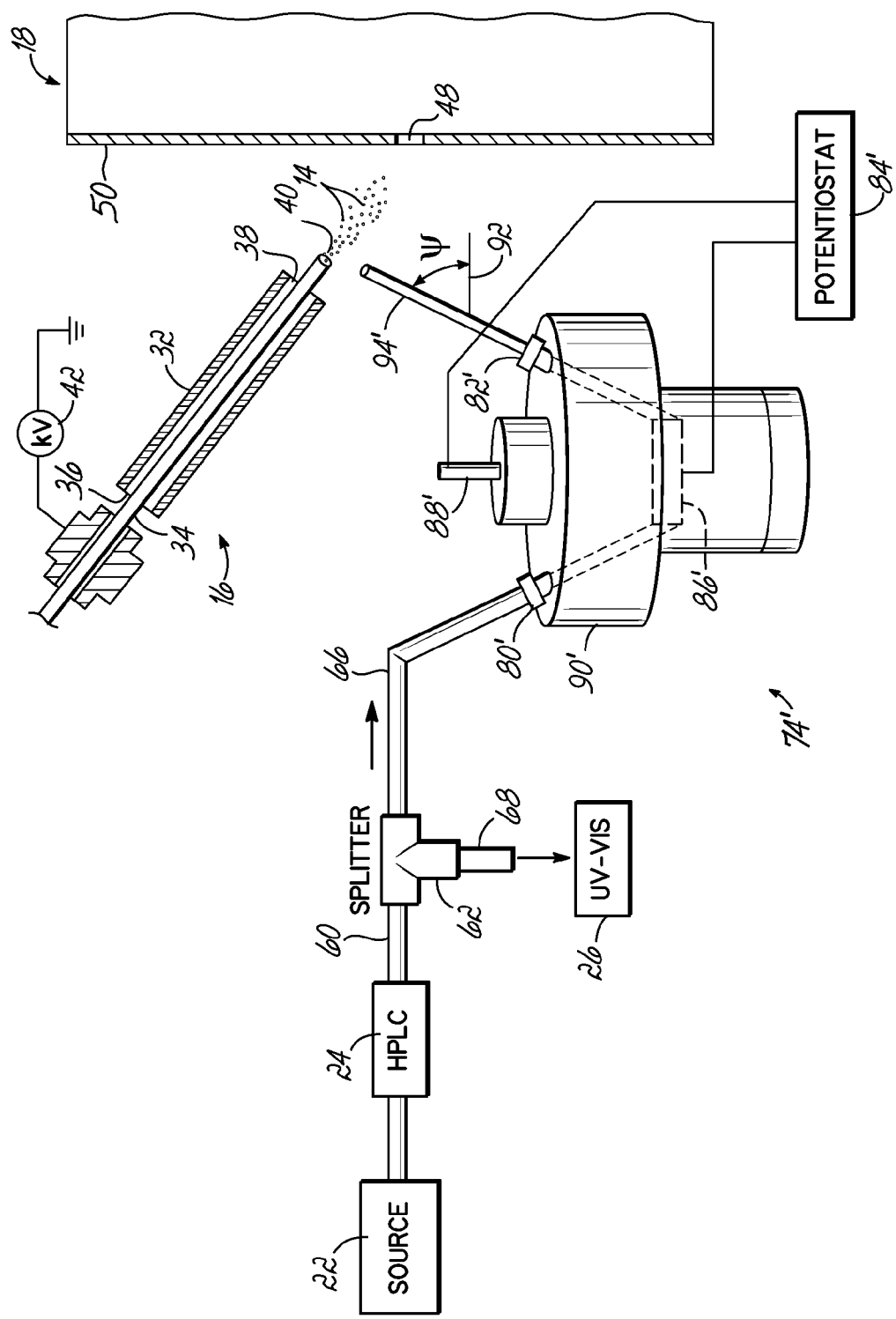
FIG. 4A is a diagrammatic depiction of a variation of the invention shown in FIG. 4, showing a commercial Reactor-cell.

Electrochemical cells are devices that are used to generate oxidized or reduced species via electrochemical reactions. In the illustrative embodiment, the electrochemical cell 74 is a thin-layer electrochemical flow cell, such as a commercially-available REACTORCELL (FIG. 4A) or μ-PREPCELL (FIG. 4) brands of thin-layer electrochemical cells available from Antec Leyden (Zoeterwoude, Netherlands); however, other types of electrochemical cells may also be used. The thin-layer electrochemical flow cell 74 includes a sample inlet 80 and a sample outlet 82 and is operably coupled to a potentiostat 84. The potentiostat 84 provides and controls the electrical voltage levels supplied to a working electrode 86, a reference electrode 88, and a counter electrode 90 of the thin-layer electrochemical flow cell 74. The working electrode 86 may be constructed from glass carbon or it may be a magic diamond ("MD") electrode Antec Leyden (Zoeterwoude, Netherlands), and the counter electrode 90 may be a titanium block.

In use, the fractions elute from the column of the HPLC 24 and are pumped into the splitter 62. The second portion may enter the UV-Vis 26 as shown herein, or the waste container 64 as shown in FIG. 2. The first portion (i.e., the liquid sample 12) enters the sample inlet 80 of the electrochemical cell 74 where the voltage potential applied by the working electrode 86 induces reduction or oxidation of a chemical species within the liquid sample 12. The liquid sample 12 with the reduced/oxidized species flows through the sample outlet 82 and into another third tube 92, which, as shown, may be angled ($\Psi$) with respect to horizontal (indicated as axis 92). The liquid sample 12 may be emitted from the third tube 92 may be directly desorbed from an opening 94 of the third tube 92. The analytes within the liquid sample 12 may then be analyzed as described previously.

Accordingly, various embodiments have been shown that a DESI probe may be configured to produce a suitable ion signal at very high sample flow rates, such as those associated with an HPLC. Additionally, derivatization of the liquid sample, such as by online reaction accompany DESI ionization (i.e., by reactive DESI), may be implemented with the DESI probe without time delays, which greatly reduces the occurrence of peak broadening in mass spectroscopy detection. Finally, the combination of liquid chromatography with a DESI probe and an electrochemical cell provides particular analytical value for achieving fast structural analysis, such as disulfide bond analysis of in peptides from enzymatic digestion.

The invention will be further appreciated in light of the following examples:

Example 1

Figure 5A:
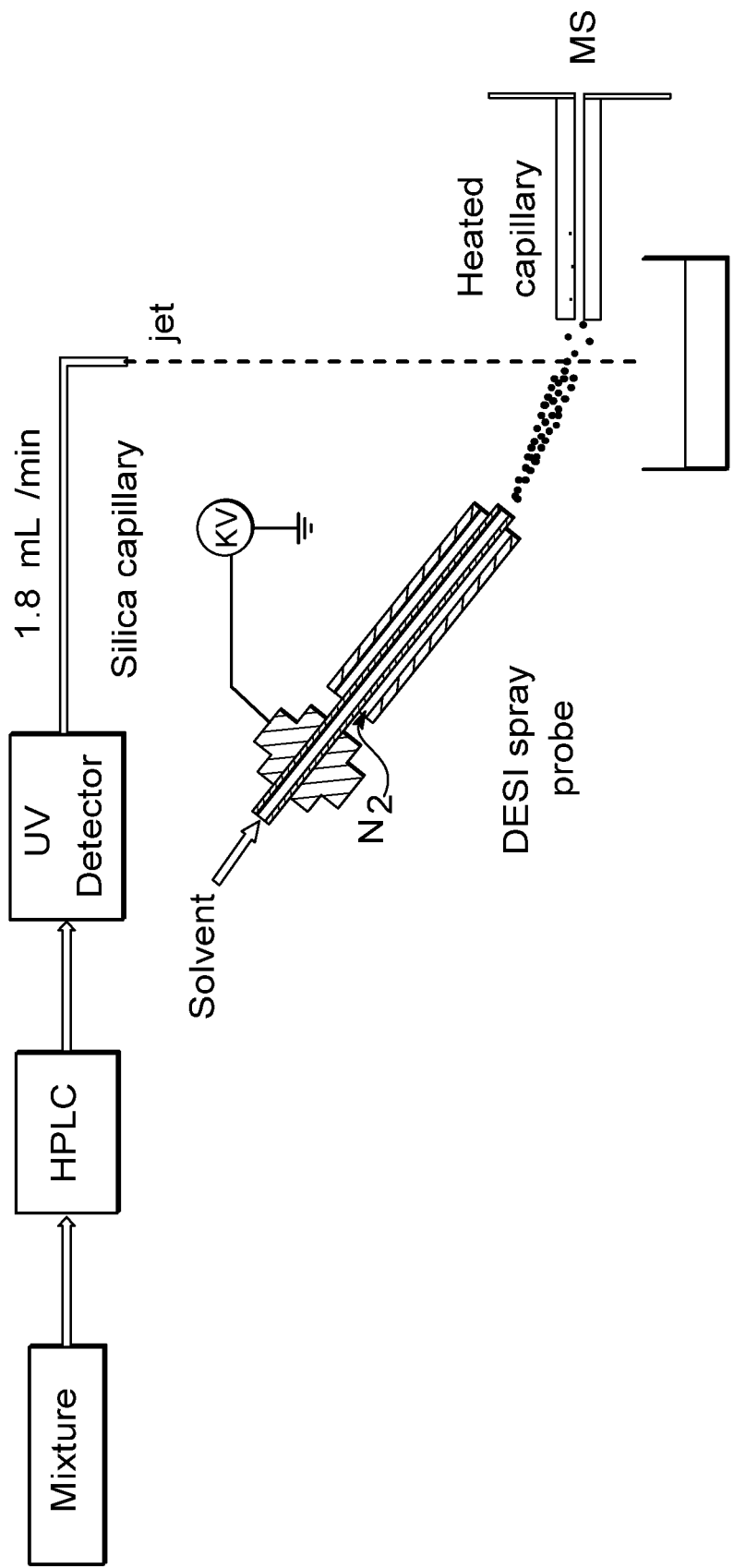
FIG. 5A is a diagrammatic depiction illustrating an alalytical system for utilizing high sample flow rate DESI-MS.

FIG. 5A illustrates an analytical system for demonstrating high sample flow rate DESI-MS that was similar to the embodiment of FIG. 1. More specifically, the system included a Thermo Finnigan LCQ DECA or DECA MAX ion trap mass spectrometer (San Jose, Calif.) and a Perkin Elmer HPLC system (Perkin Elmer, Shelton, Conn.) with an Agilent C18 column (250 mm×4.6 mm i.d.) The DESI spray voltage was set at +5 kV and the nebulizing gas ($N_2$) pressure used was 170 psi. Unless specified otherwise, the DESI spray solvent was 1% acetic acid in acetonitrile or in methanol/water (1:1 by volume) and sprayed at 10 μL/min.

A sample comprising a 10 μL mixture consisting of three neurotransmitter compounds (3 mg/mL each), norepinephrine ("NE"), normetanephrine ("NM"), and dopamine ("DA"), underwent liquid chromatography separation using an isocratic elution with the mobile phase being 50 mM aqueous ammonium formate (pH 3.0 adjusted with formic acid), flowed through the UV-Vis (detection wavelength was set at 266 nm) and then was subject to ionization by the DESI probe.

Figure 5B:
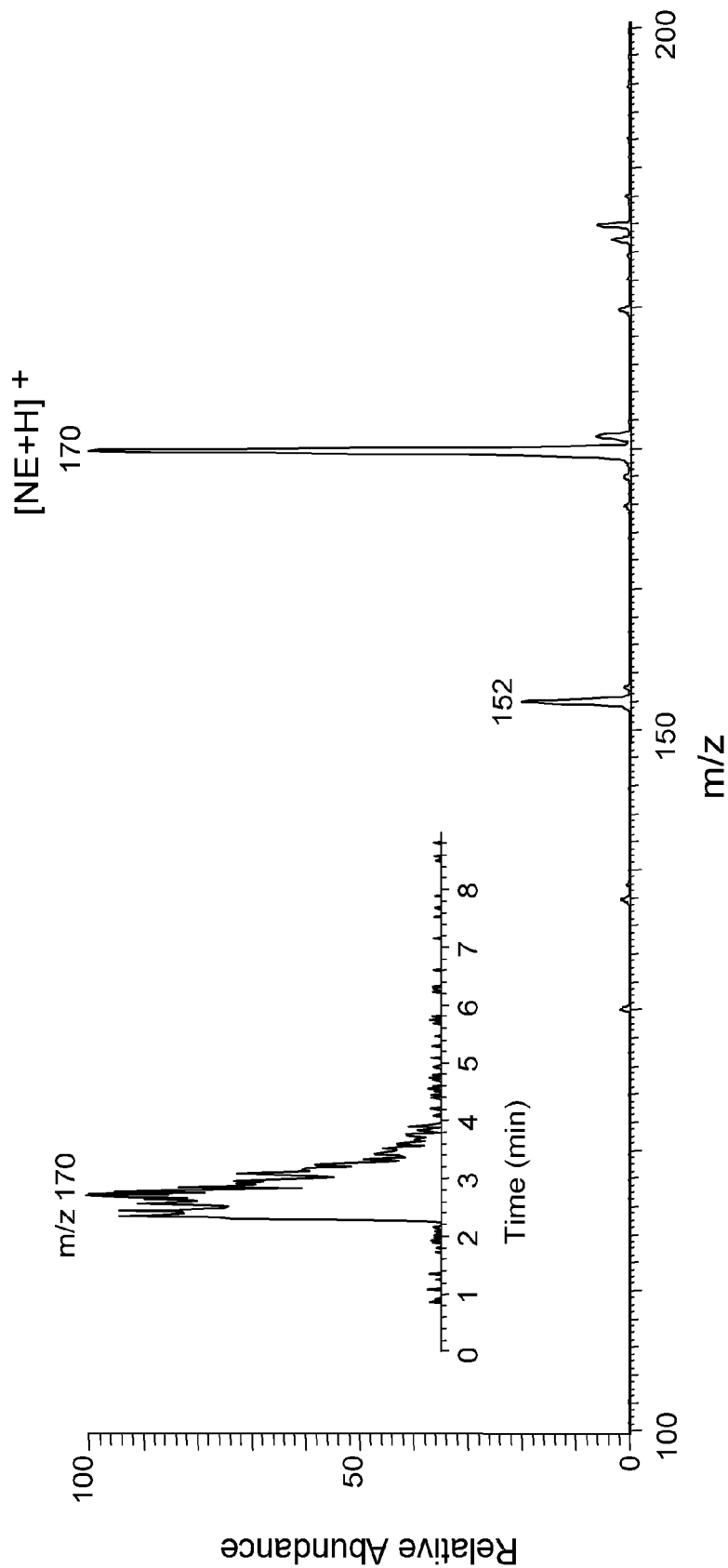
FIGS. 5B-5D are mass spectra acquired from DESI-MS.
Figure 5C:
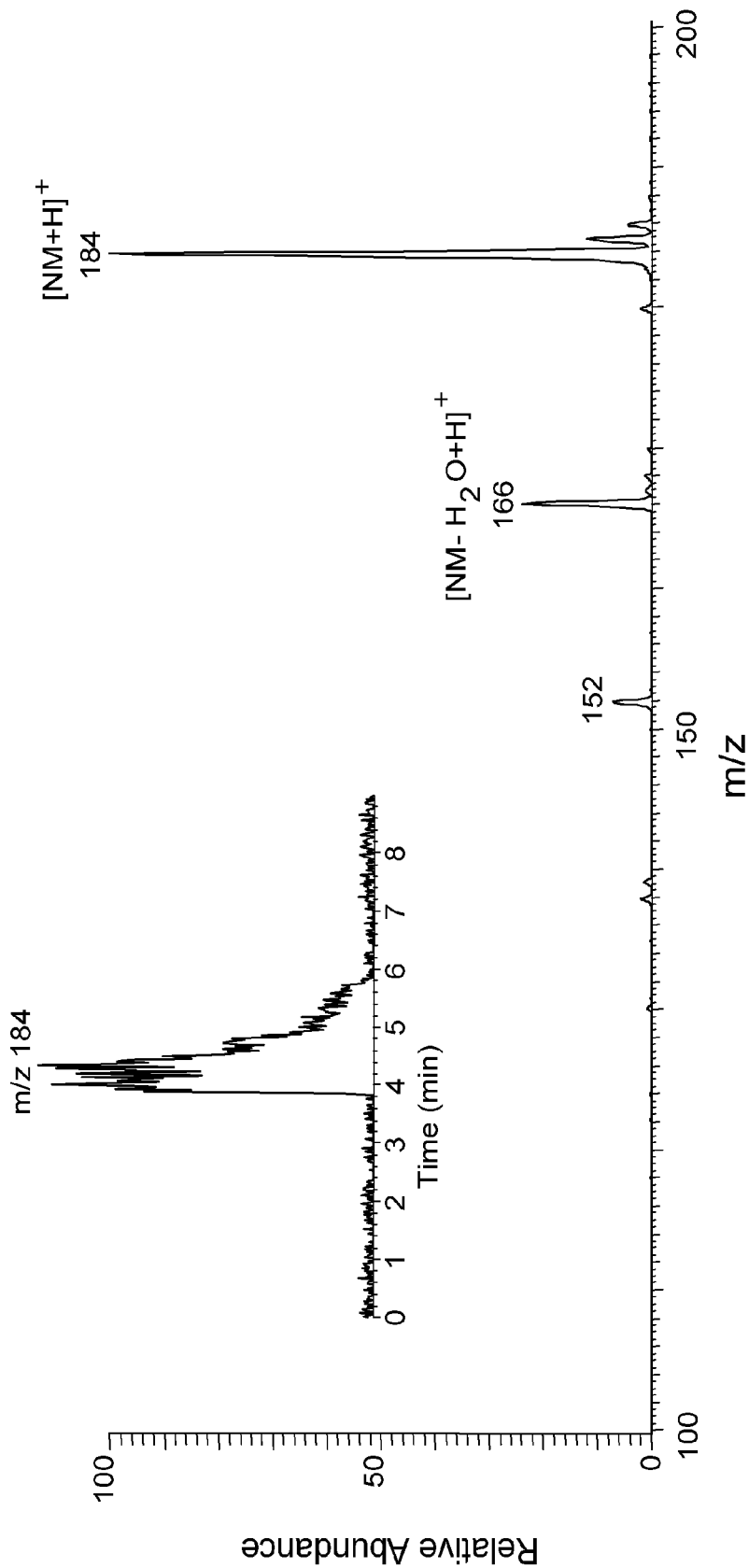
Figure 5D:
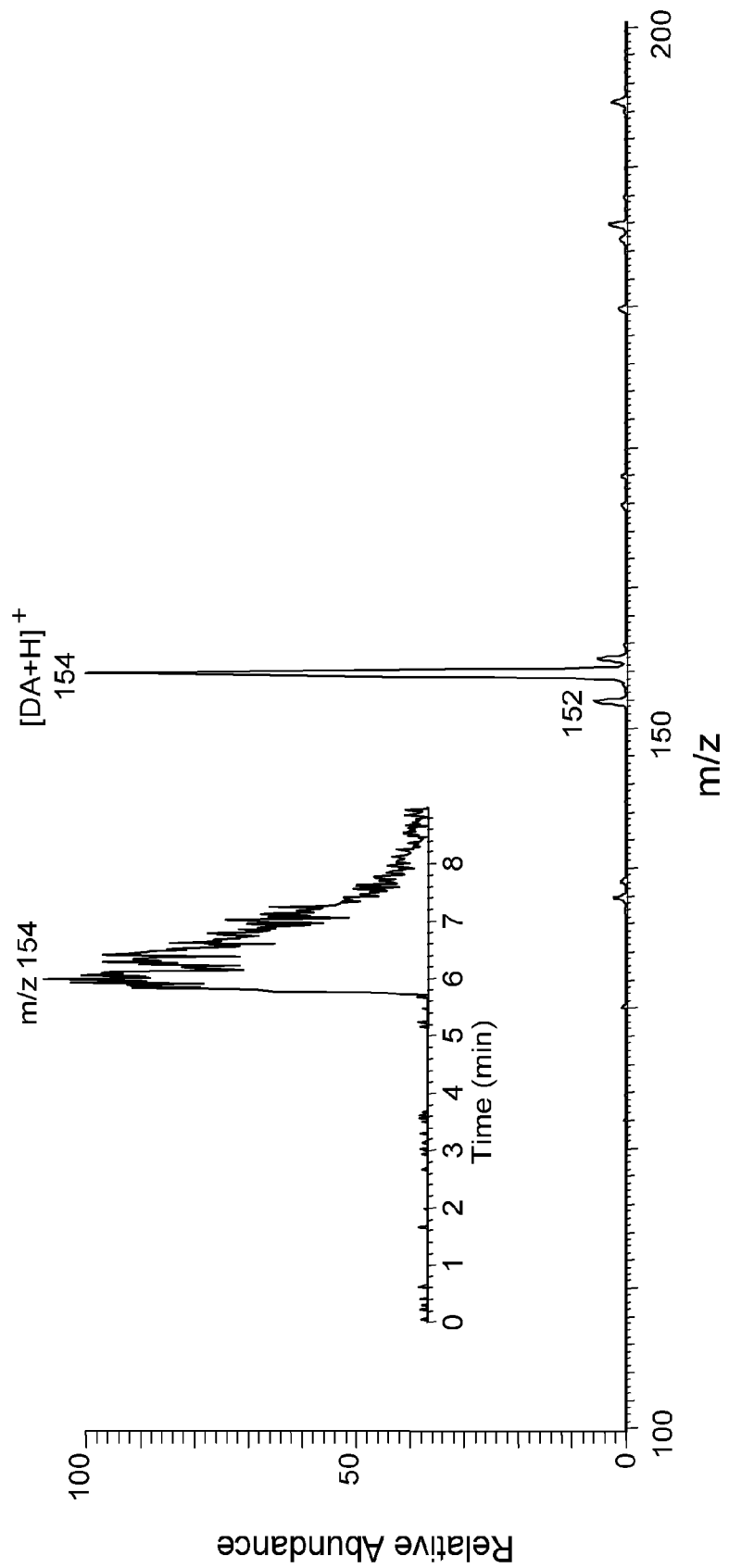

FIGS. 5B-5D illustrate the acquired DESI-MS mass spectra of the three separated NE, NM, and DA, and clearly show the corresponding protonated ions at m/z 170, 184 and 154, respectively. In addition, the extracted ion chromatograms (XICs) of m/z 170, 184 and 154 are shown in the Figure insets. These XICs agree well with the UV chromatogram and there is less than 3 s delay between the UV and DESI-MS detection, owing to the high elution flow rate used. It can also be seen that m/z 152 came from background. In FIG. 1C, m/z 166 arose from the protonated NM (m/z 184) by loss of one water molecule.

In this experiment, the aqueous eluent containing no organic solvent was ionized directly by DESI.

Example 2

Post-column derivatization in LC/MS was demonstrated using an analytical system that is similar to the embodiment shown in FIG. 3. The sample was a neurotransmitter mixture with adopted selective boronic acid chemistry for derivatization. It is known that phenylboronic acid can selectively bind cis-diol to form a stable cyclic boronate via complexation reactions. In this study, 0.1 mM N-methyl-4-pyridineboronic acid iodide in acetonitrile was used as the DESI spray solution to provide a reagent ion of the positively charged N-methyl-4-pyridineboronic acid. The permanent charge carried by the reagent ion is helpful in enhancing the sensitivity of DESI-MS analysis. Operational conditions were similar to those of Example 1 but for including an ASI adjustable splitter to reduce the flow rate to 4.5 µL/min.

Figure 6A:
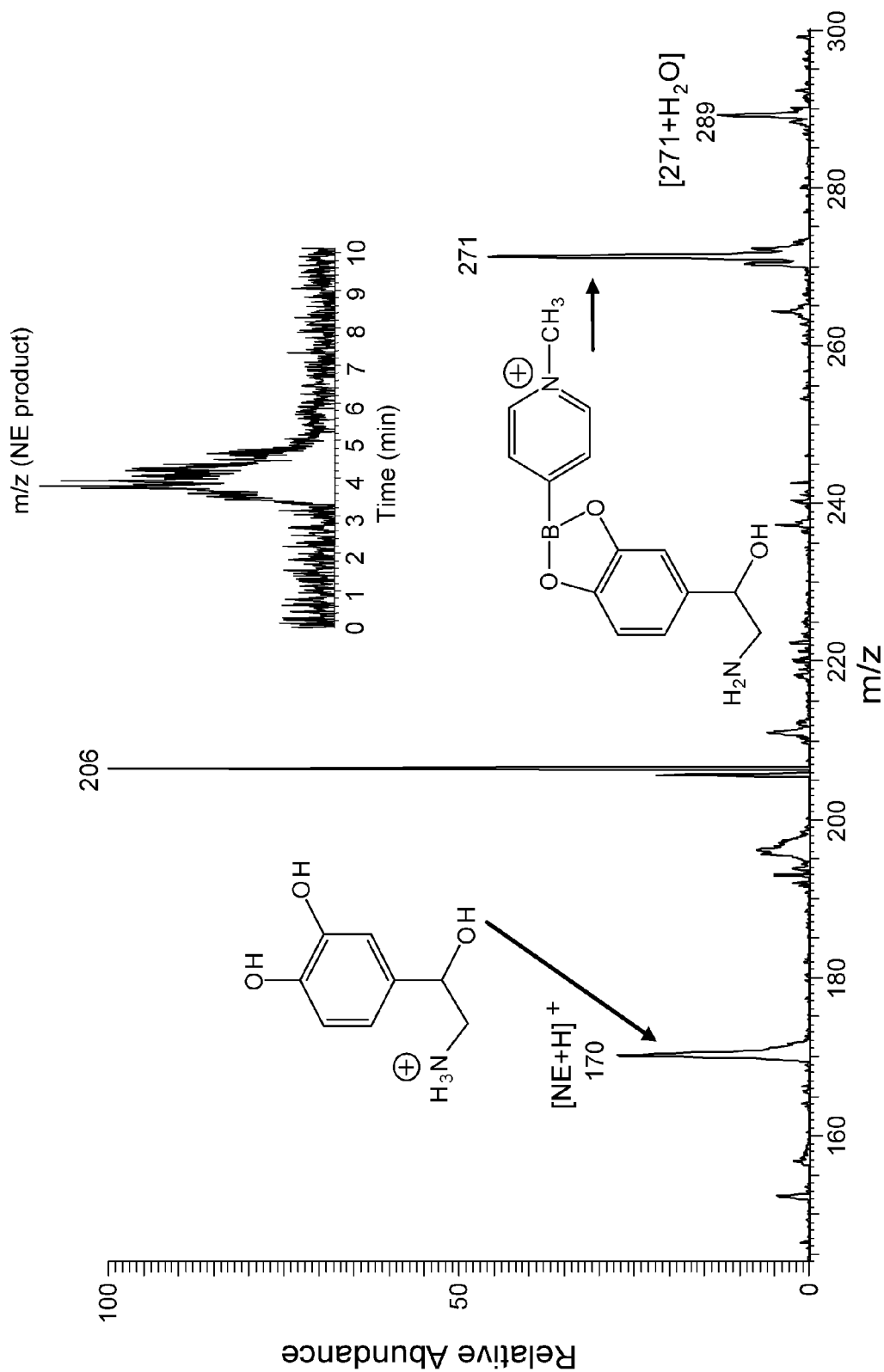
FIGS. 6A-6C are mass spectra obtained in accordance with Example 2.
Figure 6B:
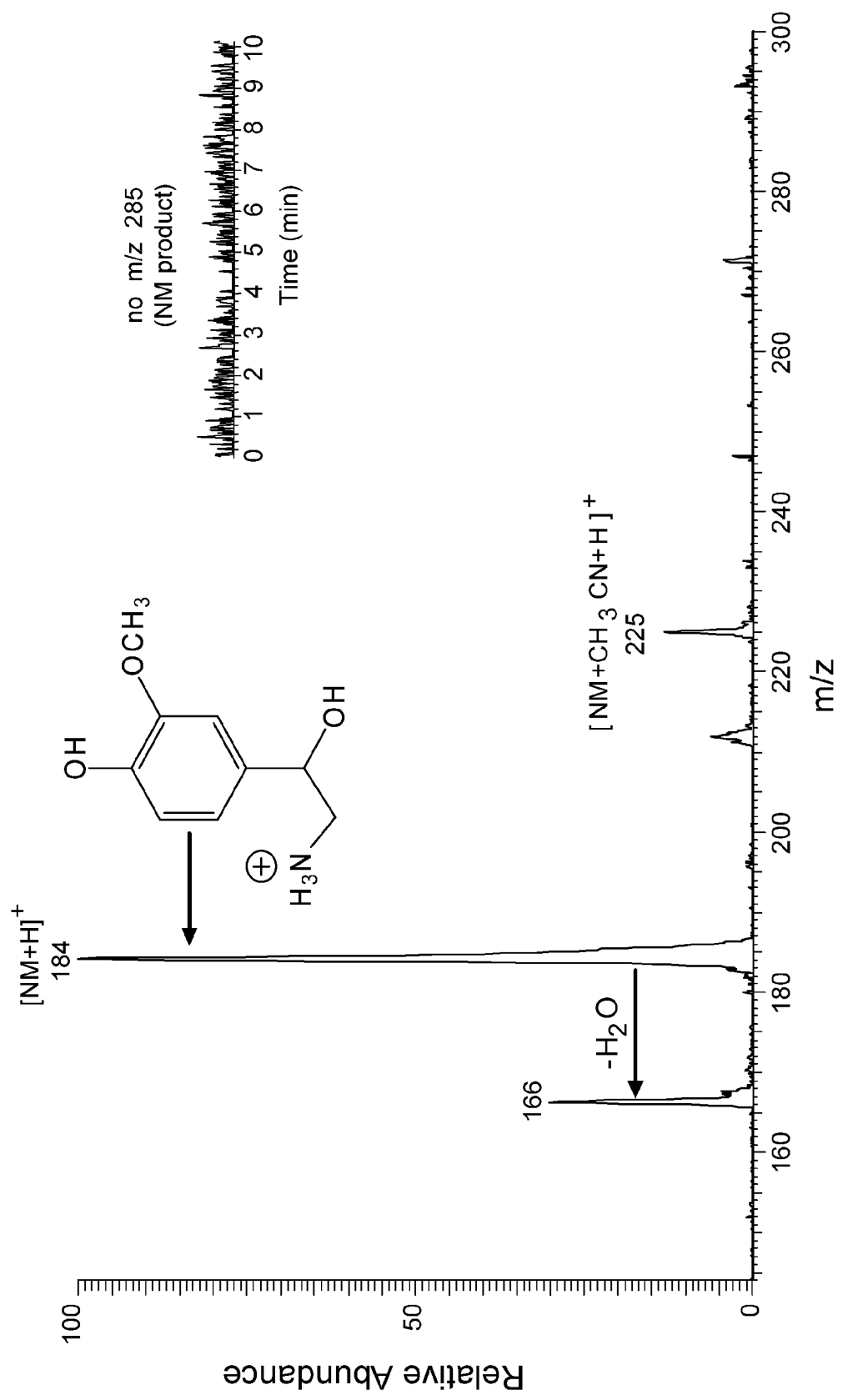
Figure 6C:
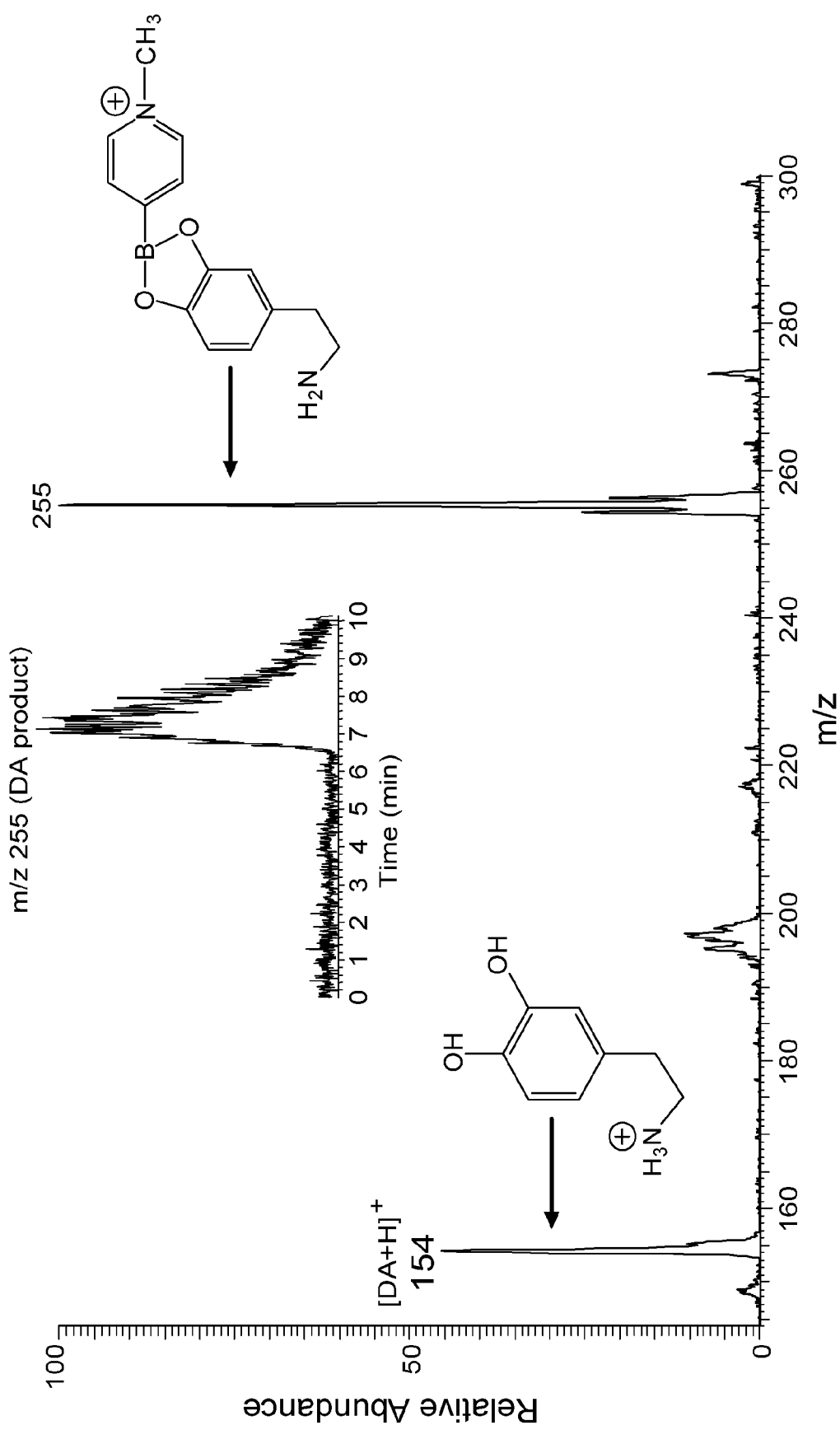

FIGS. 6A and 6C illustrate the product ions of m/z 271 and 255, arising from the complexation reactions of the reagent ions with NE and DA, respectively, via losses of two molecules of water. In contrast, no such product ion was seen for the compound NM in FIG. 6B as one of its cis-diol was methylated. Only [NM+H]$^+$ (m/z 184), [NM−H$_2$O+H]$^+$ (m/z 166) and [NM+CH$_3$CN+H]$^+$ (m/z 225) were observed. It is evident that both NE and DA containing the cis-diol functionality react with the reagent ion selectively while NM with one protonated hydroxyl group does not.

Example 3

LC/MS in conjunction with electrochemical conversion has unique applications in proteomics, such as in the fast structural elucidation of disulfide-containing peptides via online electrochemical reduction. Conventionally, disulfide linkages increase the complexity for the protein/peptide structure elucidation by MS. Thus the cleavage of disulfide bonds is often essential as dissociation of a reduced protein/peptide ion can give rise to more structurally informative fragment ions than that of the intact counterpart.

Figure 7A:
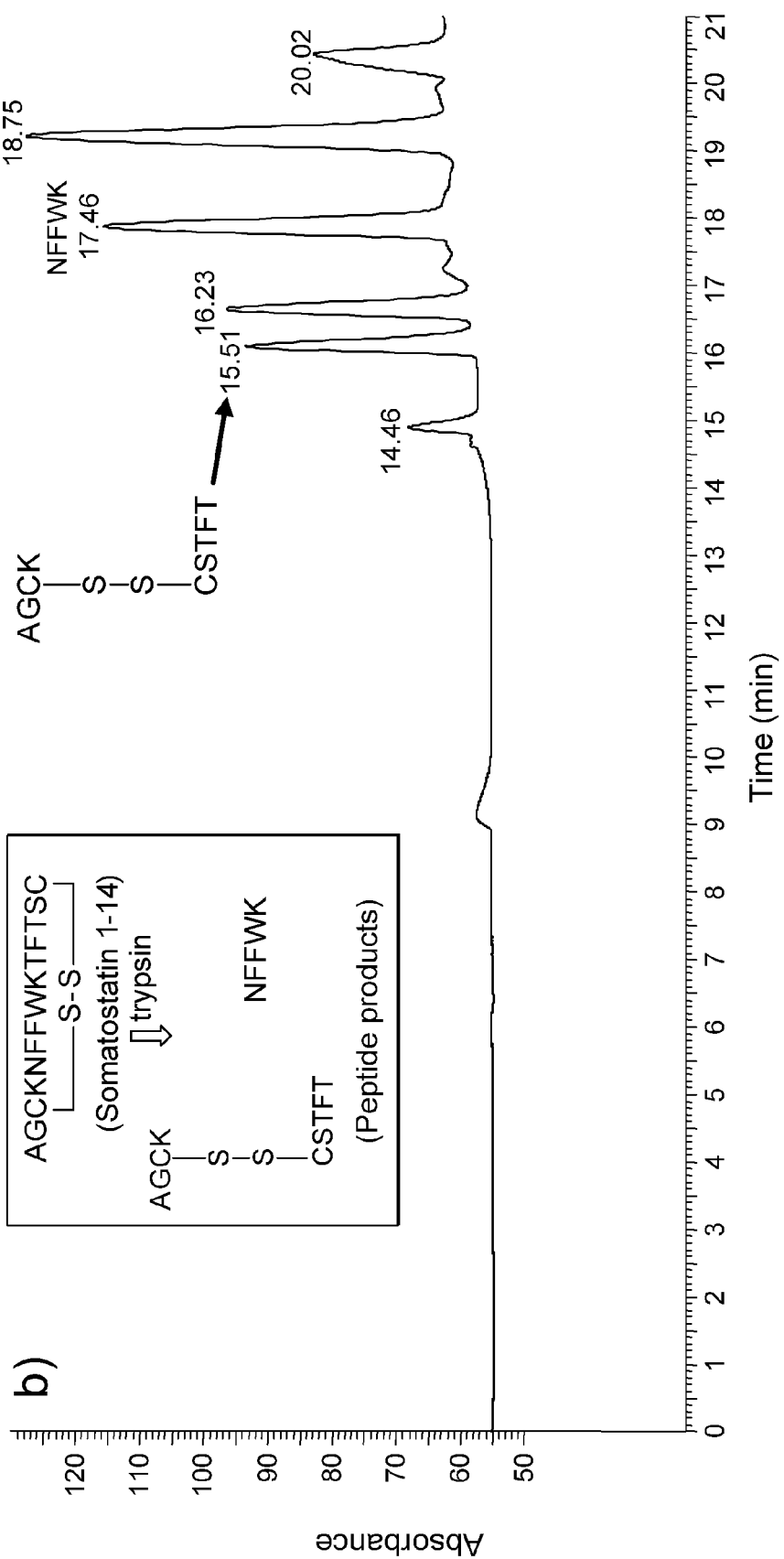
FIG. 7A is a UV chromatogram made in accordance with Example 3.
Figure 7B:
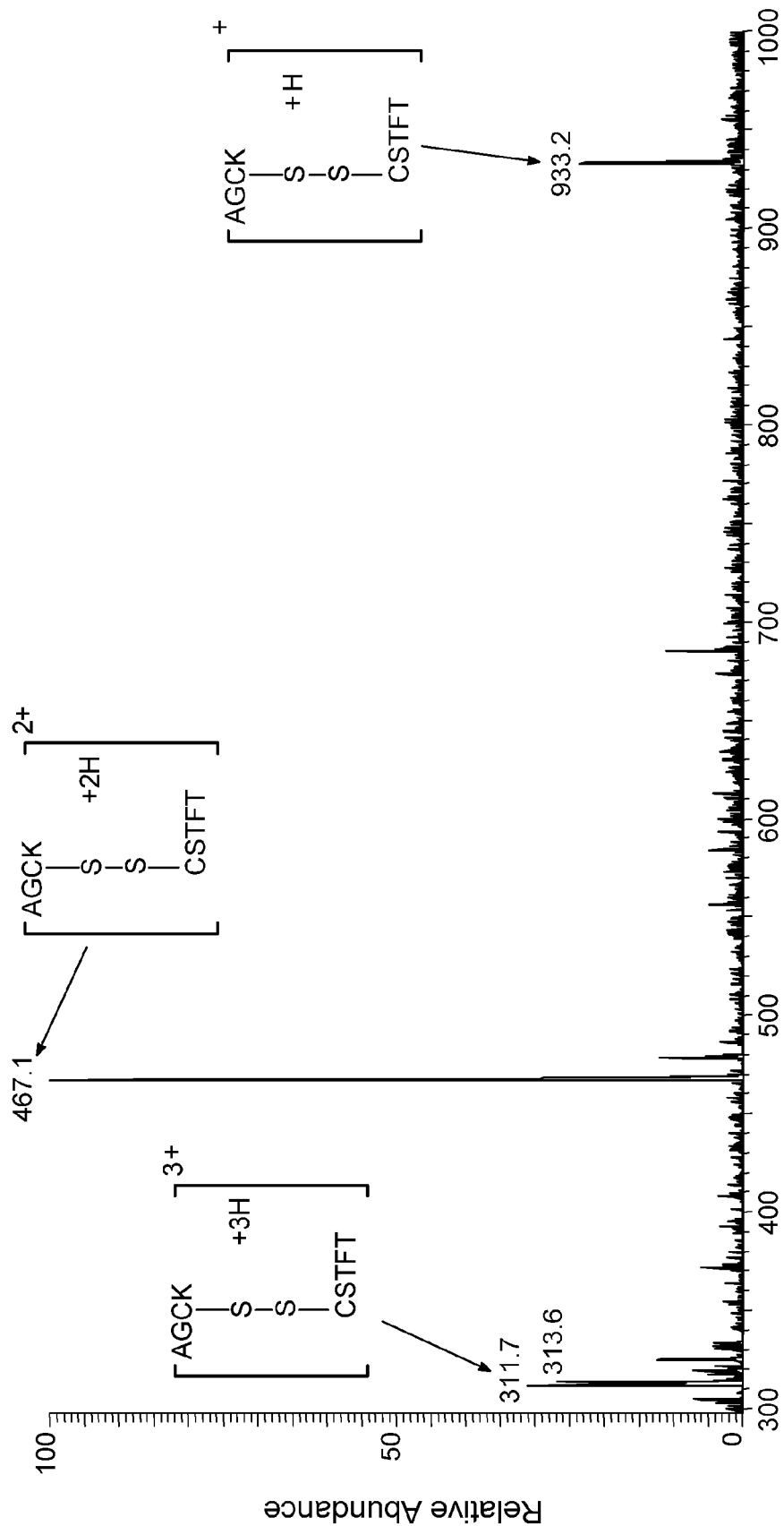
Figure 8A:
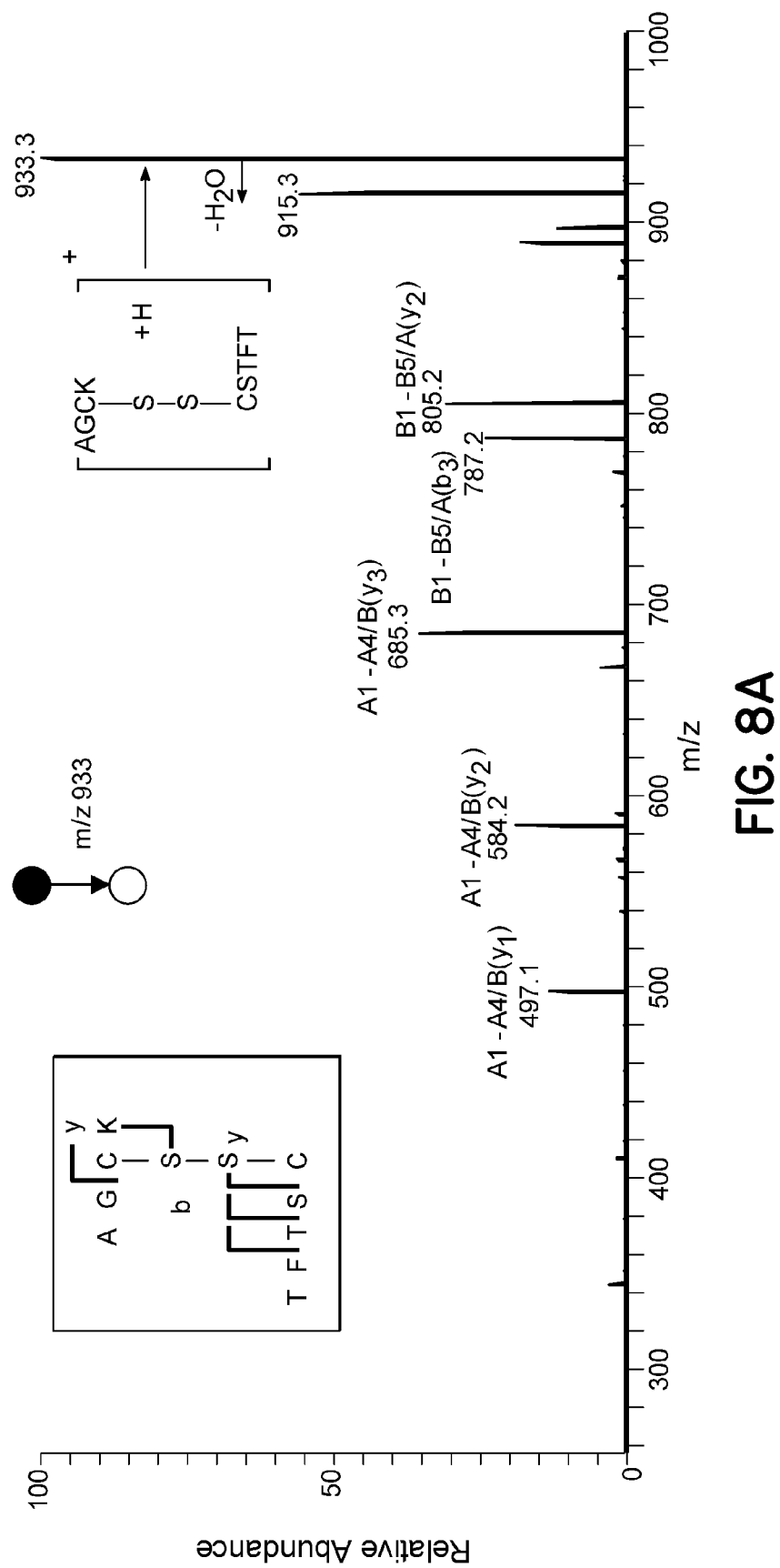
FIGS. 8A-8F are MS spectra of peptide fragments.
Figure 8B:
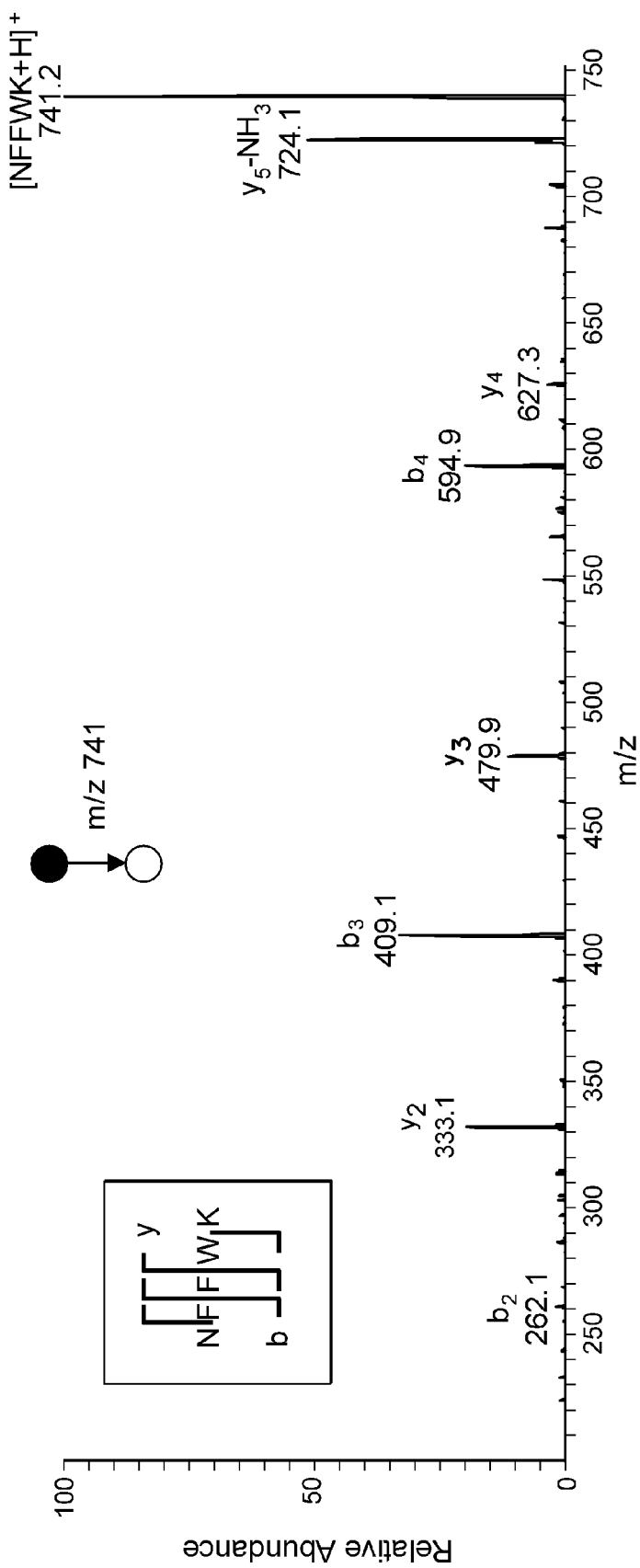

Using an analytical system that is similar to the embodiment provided in FIG. 4, a disulfide-containing peptide somatostatin 1-14 (MW 1637.9 Da) was digested by trypsin to produce a peptide mixture: AGCK/TFTSC (this peptide has two chains of AGCK and TFTSC linked by a disulfide bond), and NFFWK, the sequences of each shown in FIG. 7A. This digest mixture was examined using the analytical system. The separation of the mixture was carried out using a gradient elution. As displayed in FIG. 7A, the two peptides eluted at 15.51 min and 17.46 min, respectively (these assignments were confirmed by MS/MS spectra, shown in FIGS. 8A and 8B). Other peaks in FIG. 7A were also observed, probably originating from the trypsin used in digestion. FIG. 7B shows the DESI-MS of the peptide AGCK/TFTSC eluted at 15.51 min, when no potential applied to the cell. The singly, doubly, and triply charged peptide ions were detected at m/z 933.2, 467.1, and 311.7, respectively.

Figure 8C:
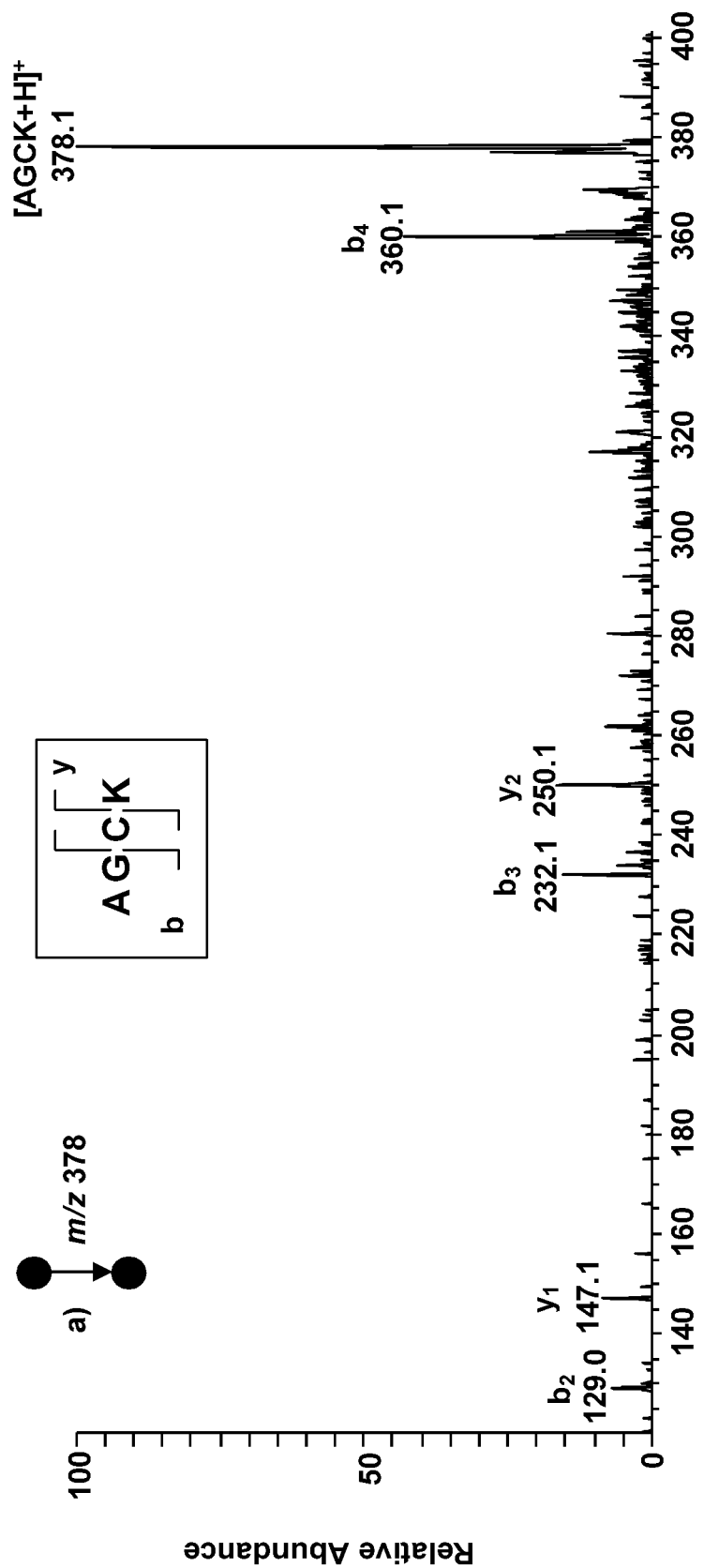
Figure 8D:
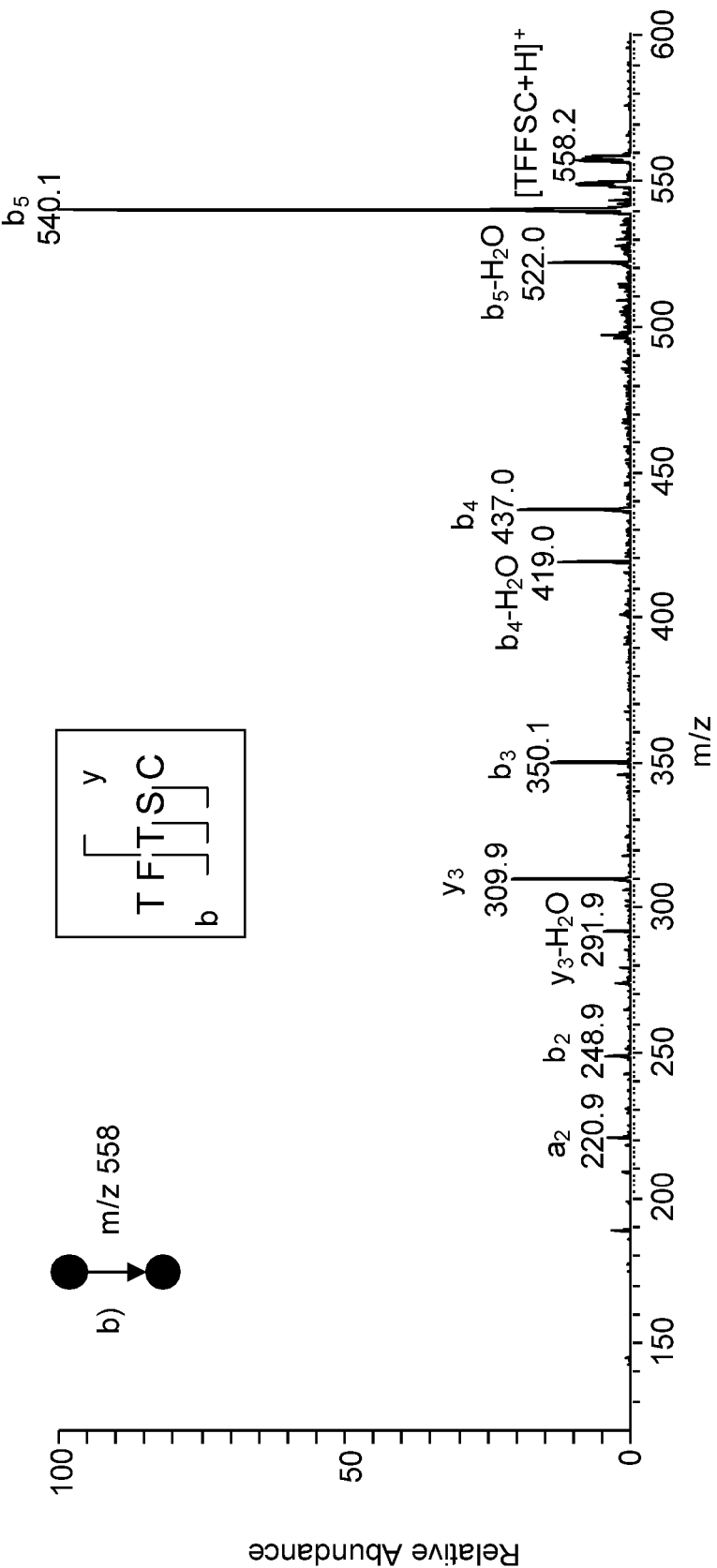
Figure 8E:
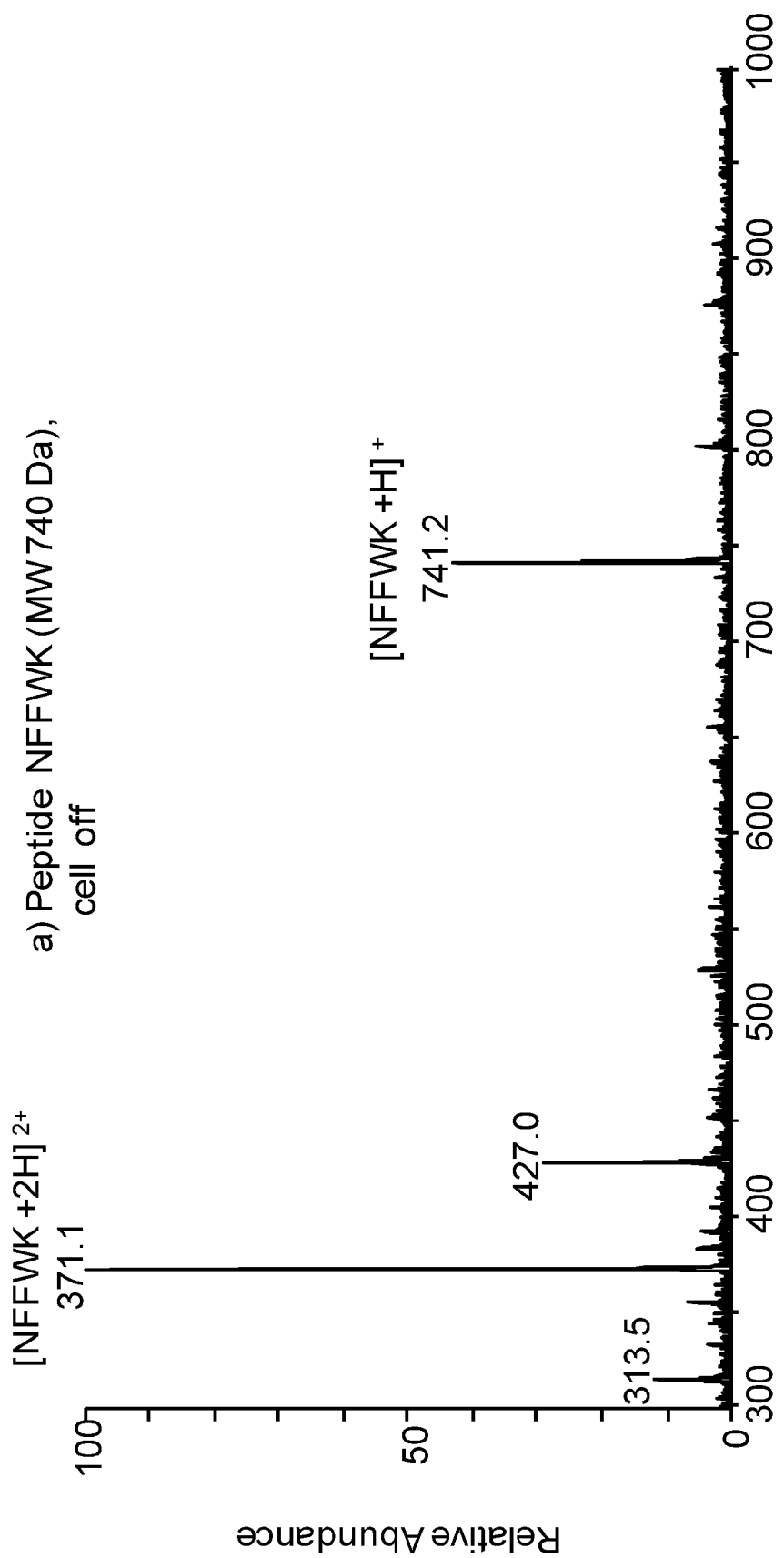
Figure 8F:
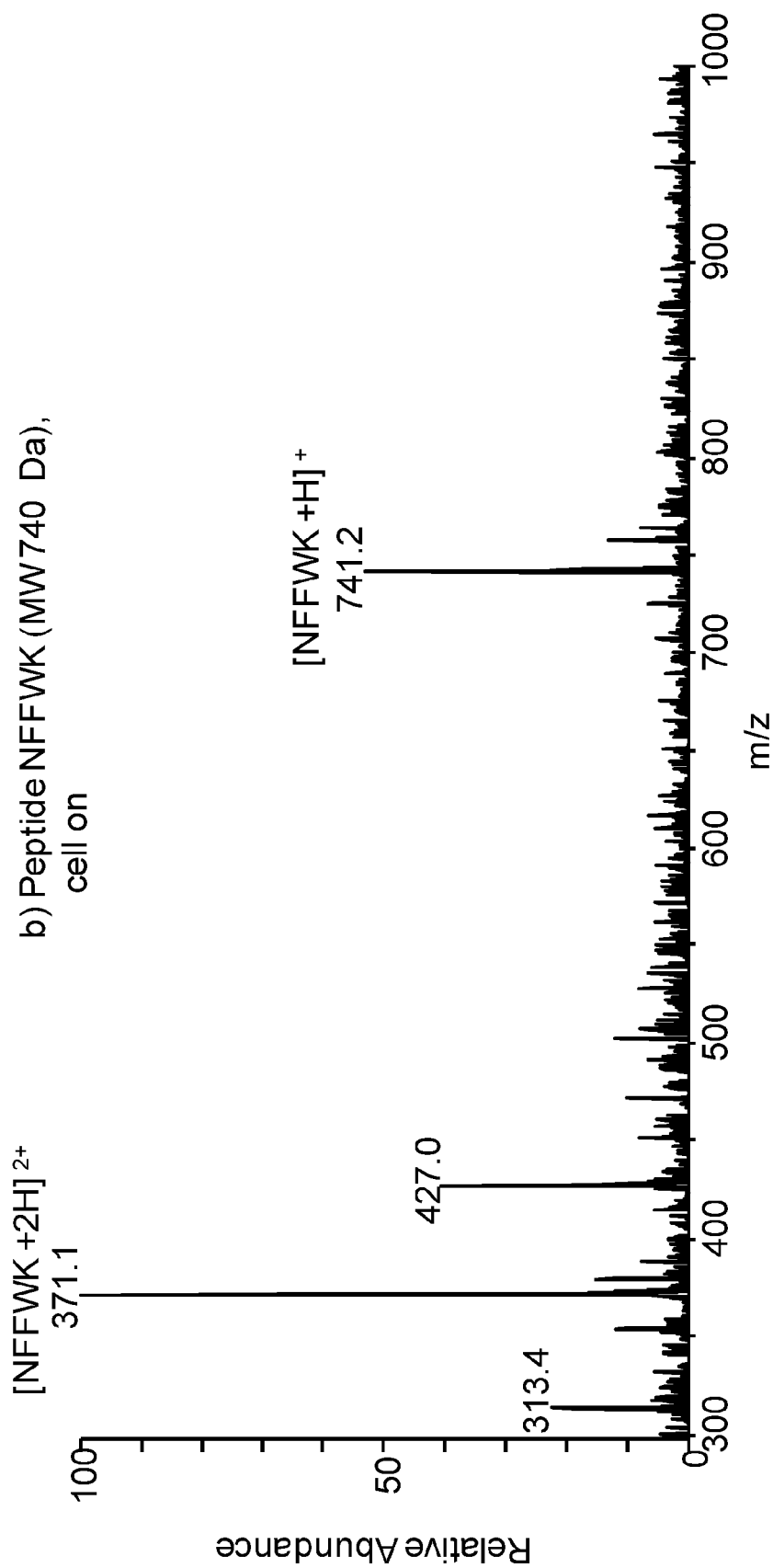

When a −1.5 V potential was applied to the cell for reduction, these peptide ion peaks disappeared, as shown in FIG. 7C, indicating a 100% reduction yield (probably due to a large MD electrode of 12×30 mm$^2$ used). Instead, two new ions of m/z 378.1 and 558.0 were observed. As the electrochemical reduction occurs after chromatographic separation, it is reliable to conclude that the two ions are from the reduction products of the AGCK/TFTSC. Indeed, they correspond to the protonated ions of two chains AGCK and TFTSC, respectively. Further, the sum of the MWs of the two products (378.1 Da+558.0 Da−2 Da=934.1 Da) is higher than that of precursor peptide (932.2 Da) by 1.9 Da, suggesting that the precursor peptide has one disulfide bond. In addition, tandem MS analysis was performed to elucidate the electro-generated ion structures, for establishing the disulfide bond connectivity as well as the sequence of the peptide AGCK/TFTSC. Upon collision induced dissociation, the m/z 378.1 gives rise to $b_2$, $b_3$, $b_4$, $y_1$, and $y_2$ fragment ions (refer to FIG. 8C), from which its sequence can be determined as either AGCK or GACK (cysteine is in 3rd position). Likewise, the m/z 558.0 dissociates into $a_2$, $b_2$, $b_3$, $b_4$-H$_2$O, $b_5$-H$_2$O, and $y_3$-H$_2$O ions (refer to FIG. 8D), which reveals its sequence to be either TFTSC or FTTSC and the cysteine residue to be the 5th position in chain. Thus it can be seen that the sole disulfide bond of AGCK/TFTSC bridges the 3rd residue of one chain with the 5th residue of the other chain. These results show that, by using the LC/EC/DESI-MS, one can obtain useful sequence information of the examined peptide and explicitly establish the connectivity of the disulfide bond. Also, the protonated peptide NFFWK containing no disulfide bond remained unchanged once the cell potential was applied, as shown in FIGS. 8E and 8F. This suggests that LC/EC/DESI can also be used to differentiate disulfide-bond containing peptides from others in an enzymatic digest.

This has been a description of the present invention along with the various methods of practicing the present invention. However, the invention itself should only be defined by the appended claims.

The invention claimed is:

1. A liquid sample analyzer comprising:
   a liquid chromatography system configured to receive a liquid sample and to separate the liquid sample into one or more fractions and emit said one or more fractions as a jet;
   a nebulizing ionizer configured to generate a charged, nebulized solvent, the nebulized solvent being directed toward said jet so as to ionize and desorb at least a portion of the liquid sample; and
   a mass analyzer configured to analyze a mass-to-charge ratio of the ionized and desorbed liquid sample.

2. The liquid sample analyzer of claim 1 further comprising:
   a splitter fluidically coupling the chromatography system to the nebulizing ionizer, wherein the splitter diverts a first volume of said one or more fractions to the nebulizing ionizer and a second volume away from the nebulizing ionizer.

3. The liquid sample analyzer of claim 2, wherein the second volume is directed to a spectrum analyzer.

4. The liquid sample analyzer of claim 1 further comprising:
   an electrochemical cell configured to receive the one or more fractions of the liquid sample and having potential bias coupled thereto that is configured to supply an energy sufficient to oxidize or reduce the one or more fractions of the liquid sample.

5. A liquid sample analyzer comprising:
a liquid chromatography system configured to receive a liquid sample and to separate the liquid sample into one or more fractions;
a splitter fluidically coupling the chromatograph to the nebulizing ionizer, wherein the splitter diverts a first volume of the liquid sample from the chromatography system as a jet to the nebulizing ionizer and a second volume away from the nebulizing ionizer;
a nebulizing ionizer configured to generate a charged, nebulized solvent, the nebulized solvent being directed toward the jet so as to ionize and desorb at least a portion of the first volume of the liquid sample; and
a mass analyzer configured to analyze a mass-to-charge ratio of the ionized and desorbed liquid sample.

6. A liquid sample analyzer comprising:
a liquid chromatography system configured to receive a liquid sample and to separate the liquid sample into one or more fractions;
a splitter fluidically coupling the chromatograph to the nebulizing ionizer, wherein the splitter diverts a first volume of the liquid sample to the nebulizing ionizer and a second volume away from the nebulizing ionizer;
an electrochemical cell configured to receive the first volume of the liquid sample and having potential bias coupled thereto that is configured to supply an energy sufficient to oxidize or reduce the first volume of the liquid sample
a nebulizing ionizer configured to generate a charged, nebulized solvent, the nebulized solvent being directed toward the oxidized or reduced first volume of the liquid sample so as to ionize and desorb at least a portion of the oxidized or reduced first volume of the liquid sample; and
a mass analyzer configured to analyze a mass-to-charge ratio of the ionized and desorbed liquid sample.

7. A method of analyzing a liquid sample, the method comprising:
separating the liquid sample into one or more fractions with a liquid chromatograph and emitting said one or more fractions as a jet;
causing the one or more fractions to undergo both derivatization and ionization by contacting said jet with a nebulized solvent containing derivatizing agents from a DESI probe; and measuring a relative abundance of at least one analyte within the ionized and desorbed derivatives.

8. A method of analyzing a liquid sample, the method comprising:
separating the liquid sample into one or more fractions with a liquid chromatograph;
splitting the one or more fractions into a first volume and a second volume;
ionizing and desorbing the first volume with a DESI probe by emitting said first volume from said liquid chromatograph and contacting said first volume with a nebulizing solvent;
analyzing a spectrum of the second volume; and
measuring a relative abundance of at least one analyte within the ionized and desorbed first volume.

9. A method of analyzing a liquid sample, the method comprising:
separating the liquid sample into one or more fractions with a liquid chromatograph;
splitting the one or more fractions into a first volume and a second volume;
causing the first volume to undergo both derivatization and ionization;
using a DESI probe;
analyzing a spectrum of the second volume; and
measuring a relative abundance of at least one analyte within the ionized and desorbed derivatives.

10. A liquid sample analyzer comprising:
a liquid chromatography system configured to receive a liquid sample and to separate the liquid sample into one or more fractions and emit said one or more fractions as a jet;
an ionizer configured to ionize at least a portion of the liquid sample at least one or more fractions; and
a mass analyzer configured to analyze a mass-to-charge ratio of the ionized and desorbed liquid sample.

11. The liquid sample analyzer of claim 10, wherein the ionizer is a nebulizing ionizer configured to generate a charged, nebulized solvent, the nebulized solvent being directed toward the liquid sample so as to desorb the least a portion of the liquid sample.

12. The liquid sample analyzer of claim 10, wherein the ionizer is a charged needle, a laser beam, a plurality of excited atoms, a plurality of energetic ions, a plasma, or a plurality of high-energy particles.

* * * * *

UNITED STATES PATENT AND TRADEMARK OFFICE
CERTIFICATE OF CORRECTION

PATENT NO. : 8,648,297 B2
APPLICATION NO. : 13/553145
DATED : February 11, 2014
INVENTOR(S) : Hao Chen et al.

Page 1 of 1

It is certified that error appears in the above-identified patent and that said Letters Patent is hereby corrected as shown below:

In the Specification:

Column 1, line 13, please add the following paragraph:

"This invention was made with government support under CHE1149367 awarded by the National Science Foundation. The government has certain rights in the invention."

Signed and Sealed this
Second Day of August, 2016

Michelle K. Lee
*Director of the United States Patent and Trademark Office*